United States Patent [19]
Holmes

[11] Patent Number: 5,770,456
[45] Date of Patent: Jun. 23, 1998

US005770456A

[54] CYCLIC NUCLEIC ACID AND POLYPEPTIDE ARRAYS

[75] Inventor: Christopher P. Holmes, Saratoga, Calif.

[73] Assignee: Affymetrix, Inc., Santa Clara, Calif.

[21] Appl. No.: 647,618

[22] Filed: May 13, 1996

Related U.S. Application Data

[63] Continuation of Ser. No. 972,007, Nov. 5, 1992, Pat. No. 5,527,681, which is a continuation-in-part of Ser. No. 796,727, Nov. 22, 1991, Pat. No. 5,242,974, and Ser. No. 805,727, Dec. 6, 1991, Pat. No. 5,424,186, which is a continuation-in-part of Ser. No. 624,120, Dec. 6, 1990, abandoned, which is a continuation-in-part of Ser. No. 492,462, Mar. 7, 1990, Pat. No. 5,143,854, which is a continuation-in-part of Ser. No. 362,901, Jun. 7, 1989, abandoned.

[51] Int. Cl.$^6$ .......................... G01N 33/534; C07H 19/06
[52] U.S. Cl. ........................ 436/518; 525/54.11; 530/334; 536/25.3; 536/25.31; 536/25.32; 536/126
[58] Field of Search ........................ 530/334; 525/54.11; 536/25.3–25.34, 126, 25.31; 436/518

[56] References Cited

U.S. PATENT DOCUMENTS

| | | | |
|---|---|---|---|
| 4,562,157 | 12/1985 | Lowe et al. | 435/291 |
| 4,631,211 | 12/1986 | Houghten | 428/35 |
| 5,081,584 | 1/1992 | Omichinski et al. | 364/497 |
| 5,143,854 | 9/1992 | Pirrung et al. | 436/518 |
| 5,242,974 | 9/1993 | Holmes | 525/54.11 |
| 5,556,961 | 9/1996 | Foote et al. | |

FOREIGN PATENT DOCUMENTS

| | | | |
|---|---|---|---|
| WO 86/00991 | 2/1986 | WIPO . | |
| WO 89/10977 | 11/1989 | WIPO | C12Q 1/68 |
| WO 90/03382 | 4/1990 | WIPO | C07H 21/00 |
| WO 90/15070 | 12/1990 | WIPO . | |

OTHER PUBLICATIONS

Ajayaghosh et al., "Polymer–Supported Synthesis of Protected Peptide Segments on a Photosensitive o–Nitro(α–methyl)bromo–benzyl Resin," *Tetrahedron*, 44:6661–6666 (1988).

Applied Biosystems, *Model 431A Peptide Synthesizer User's Manual*, Sections 2 and 6, Aug. 15, 1989.

Fodor et al., "Light–Directed, Spatially Addressable parallel Chemical Synthesis," *Science*, 251:767–777 (1991).

Furka et al., "General Method for Rapid Synthesis of Multi–component Peptide Mixtures," *Int. J. Peptide Protein Res.*, 37:487–493 (1991).

Geysen et al., "Strategies for epitope analysis using peptide synthesis," *J. Immunol. Meth.*, 102:259–274 (1987).

Haridasan et al., "Peptide Synthesis Using Photolytically Cleavable 2–Nitrobenzyloxycarbonyl Protecting Group," *PNAS*, 53:717–728 (1987).

Hellberg et al., "Minimum analogue peptide sets (MAPS) for quantitative structure activity relationships," *Int. J. Peptide Protein Res.*, 414–424 (1991).

Kates et al., "A Novel, Convenient, Three–Dimensional Orthogonal Strategy for Solid–Phase Synthesis of Cyclic Peptides," *Tetrahedron Letters*, 34:1549–1552 (1993).

(List continued on next page.)

*Primary Examiner*—Carol A. Spiegel
*Attorney, Agent, or Firm*—Townsend & Townsend & Crew

[57] ABSTRACT

A synthetic strategy for the creation of large scale chemical diversity. Solid-phase chemistry, photolabile protecting groups, and photolithography are used to achieve light-directed spatially-addressable parallel chemical synthesis. In one particular embodiment, an array of rotated cyclic polymers is formed. In another embodiment, an array of polymers is formed based on a target polymer. The array includes systematically substituted versions of the target molecule. In another embodiment, rotated and systematically substituted cyclic polymers are formed on a substrate.

10 Claims, 12 Drawing Sheets

OTHER PUBLICATIONS

Patchornick et al., "Photosensitive Protecting Groups," *J. Ameri. Chem. Soc.*, 92:6333–6335 (1970).

Rovero et al., "Synthesis of Cyclic Peptides on a Solid Support," *Tetrahedron Letters*, 32:2639 (1991).

Sze/McGillis, *VLSI Technology*, Chapter 7, pp. 267–301, McGraw–Hill, (1983).

Trzeciak et al., "Synthesis of 'Head–to–Tail' Cyclized Peptides on Solid Support by FMOC Chemistry," *Tetrahedron Letters*, 33:4557–4560 (1992).

Gilon et al., "Backbone Cyclization: A New Method for Conferring Conformational Constraint on Peptides," Biopolymers 31(6):745–750, 1991.

Ploax et al., "Cyclization of Peptides on a Solid Support," Int. J. Peptide Protein Res. 29: 162–169, 1987.

McMurray, "Solid Phase Synthesis of a Cyclic Peptide Using FMOC Chemistry," Tetrahedron Letters, 32(52):7679–7682, 1991.

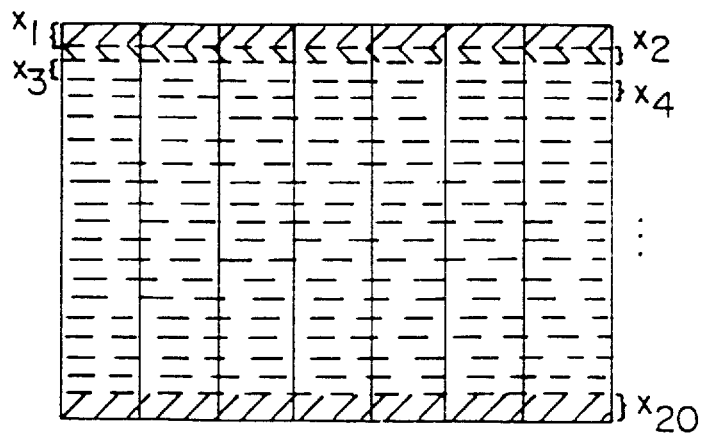
FIG. 7A.
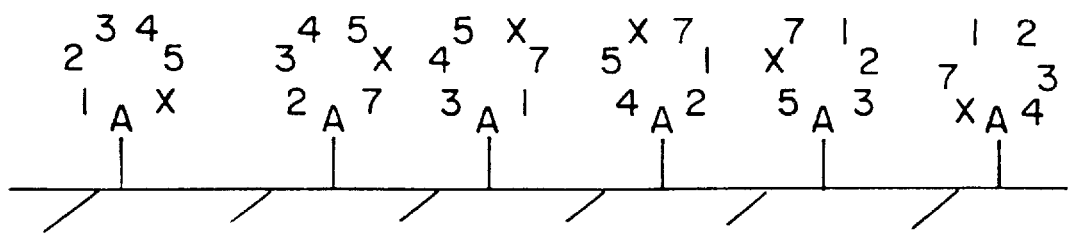
FIG. 7B.
FIG. 7C.

DONOR QUENCHER
  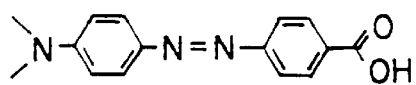
FIG. 13A.
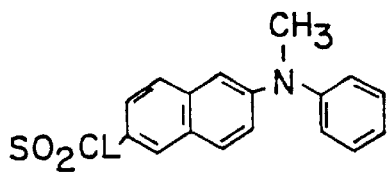  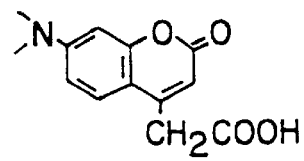
FIG. 13B.  FIG. 13C.
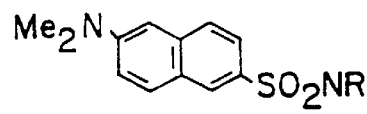  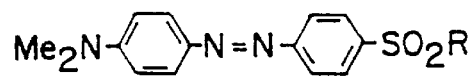
FIG. 13D.
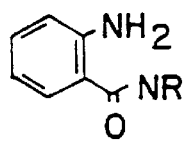  NBD-NR
FIG. 13E.
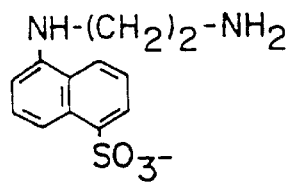  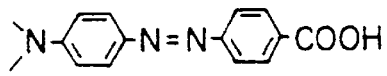
FIG. 13F.
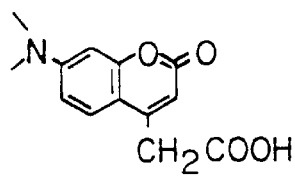
DACYL WITH PHOTOLABILE PROTECTING GROUPS AT 450 NM OR HIGHER
FIG. 13G.
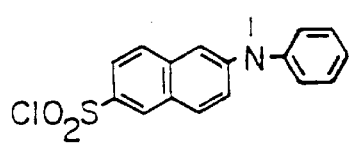
DACYL WITH PHOTOLABILE PROTECTING GROUPS AT 450 NM OR HIGHER
FIG. 13H.

5,770,456

SEQUENCE LISTING ( 1 ) GENERAL INFORMATION:

( i i i ) NUMBER OF SEQUENCES: 36

( 2 ) INFORMATION FOR SEQ ID NO:1:

( i ) SEQUENCE CHARACTERISTICS:
      ( A ) LENGTH: 10 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:1:

```
Phe  Leu  Arg  Arg  Gln  Phe  Lys  Val  Val  Thr
 1                  5                        10
```

( 2 ) INFORMATION FOR SEQ ID NO:2:

( i ) SEQUENCE CHARACTERISTICS:
      ( A ) LENGTH: 9 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:2:

```
Phe  Leu  Arg  Gln  Phe  Lys  Val  Val  Thr
 1             5
```

( 2 ) INFORMATION FOR SEQ ID NO:3:

( i ) SEQUENCE CHARACTERISTICS:
      ( A ) LENGTH: 13 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:3:

```
Tyr  Gly  Gly  Phe  Leu  Arg  Arg  Gln  Phe  Lys  Val  Val  Thr
 1                  5                        10
```

( 2 ) INFORMATION FOR SEQ ID NO:4:

( i ) SEQUENCE CHARACTERISTICS:
      ( A ) LENGTH: 8 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:4:

```
Phe  Arg  Gln  Phe  Lys  Val  Val  Thr
 1                  5
```

( 2 ) INFORMATION FOR SEQ ID NO:5:

( i ) SEQUENCE CHARACTERISTICS:
      ( A ) LENGTH: 7 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:5:

Arg Gln Phe Lys Val Val Thr
1               5

( 2 ) INFORMATION FOR SEQ ID NO:6:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:6:

Leu Arg Arg Gln Phe Lys Val Val Thr
1               5

( 2 ) INFORMATION FOR SEQ ID NO:7:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:7:

Phe Leu Arg Arg Gln Phe Lys Val Val
1               5

( 2 ) INFORMATION FOR SEQ ID NO:8:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:8:

Arg Arg Gln Phe Lys Val Val Thr
1               5

( 2 ) INFORMATION FOR SEQ ID NO:9:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:9:

Leu Arg Arg Gln Phe Lys Val Val
1               5

( 2 ) INFORMATION FOR SEQ ID NO:10:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear (i i) MOLECULE TYPE: peptide (x i) SEQUENCE DESCRIPTION: SEQ ID NO:10:

Phe Leu Arg Arg Gln Phe Lys Val
1               5

(2) INFORMATION FOR SEQ ID NO:11:

(i) SEQUENCE CHARACTERISTICS:
      (A) LENGTH: 7 amino acids
      (B) TYPE: amino acid
      (C) STRANDEDNESS: single
      (D) TOPOLOGY: linear (i i) MOLECULE TYPE: peptide (x i) SEQUENCE DESCRIPTION: SEQ ID NO:11:

Arg Gln Phe Lys Val Val Thr
1               5

(2) INFORMATION FOR SEQ ID NO:12:

(i) SEQUENCE CHARACTERISTICS:
      (A) LENGTH: 7 amino acids
      (B) TYPE: amino acid
      (C) STRANDEDNESS: single
      (D) TOPOLOGY: linear (i i) MOLECULE TYPE: peptide (x i) SEQUENCE DESCRIPTION: SEQ ID NO:12:

Arg Arg Gln Phe Lys Val Val
1               5

(2) INFORMATION FOR SEQ ID NO:13:

(i) SEQUENCE CHARACTERISTICS:
      (A) LENGTH: 7 amino acids
      (B) TYPE: amino acid
      (C) STRANDEDNESS: single
      (D) TOPOLOGY: linear (i i) MOLECULE TYPE: peptide (x i) SEQUENCE DESCRIPTION: SEQ ID NO:13:

Leu Arg Arg Gln Phe Lys Val
1               5

(2) INFORMATION FOR SEQ ID NO:14:

(i) SEQUENCE CHARACTERISTICS:
      (A) LENGTH: 7 amino acids
      (B) TYPE: amino acid
      (C) STRANDEDNESS: single
      (D) TOPOLOGY: linear (i i) MOLECULE TYPE: peptide (x i) SEQUENCE DESCRIPTION: SEQ ID NO:14:

Phe Leu Arg Arg Gln Phe Lys
1               5

(2) INFORMATION FOR SEQ ID NO:15:

(i) SEQUENCE CHARACTERISTICS:
      (A) LENGTH: 6 amino acids
      (B) TYPE: amino acid
      (C) STRANDEDNESS: single
      (D) TOPOLOGY: linear ( i i ) MOLECULE TYPE: peptide ( x i ) SEQUENCE DESCRIPTION: SEQ ID NO:15:

Gln Phe Lys Val Val Thr
1               5

( 2 ) INFORMATION FOR SEQ ID NO:16:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:16:

Arg Gln Phe Lys Val Val
1               5

( 2 ) INFORMATION FOR SEQ ID NO:17:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:17:

Arg Arg Gln Phe Lys Val
1               5

( 2 ) INFORMATION FOR SEQ ID NO:18:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:18:

Leu Arg Arg Gln Phe Lys
1               5

( 2 ) INFORMATION FOR SEQ ID NO:19:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:19:

Phe Leu Arg Arg Gln Phe
1               5

( 2 ) INFORMATION FOR SEQ ID NO:20:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:20:

Phe Lys Val Val Thr
1               5

( 2 ) INFORMATION FOR SEQ ID NO:21:

( i ) SEQUENCE CHARACTERISTICS:
      ( A ) LENGTH: 5 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:21:

Gln Phe Lys Val Val
1               5

( 2 ) INFORMATION FOR SEQ ID NO:22:

( i ) SEQUENCE CHARACTERISTICS:
      ( A ) LENGTH: 5 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:22:

Arg Gln Phe Lys Val
1               5

( 2 ) INFORMATION FOR SEQ ID NO:23:

( i ) SEQUENCE CHARACTERISTICS:
      ( A ) LENGTH: 5 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:23:

Arg Arg Gln Phe Lys
1               5

( 2 ) INFORMATION FOR SEQ ID NO:24:

( i ) SEQUENCE CHARACTERISTICS:
      ( A ) LENGTH: 5 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:24:

Leu Arg Arg Gln Phe
1               5

( 2 ) INFORMATION FOR SEQ ID NO:25:

( i ) SEQUENCE CHARACTERISTICS:
      ( A ) LENGTH: 5 amino acids
      ( B ) TYPE: amino acid
      ( C ) STRANDEDNESS: single
      ( D ) TOPOLOGY: linear (i i) MOLECULE TYPE: peptide (x i) SEQUENCE DESCRIPTION: SEQ ID NO:25:

Phe Leu Arg Arg Gln
1               5

(2) INFORMATION FOR SEQ ID NO:26:

(i) SEQUENCE CHARACTERISTICS:
      (A) LENGTH: 4 amino acids
      (B) TYPE: amino acid
      (C) STRANDEDNESS: single
      (D) TOPOLOGY: linear (i i) MOLECULE TYPE: peptide (x i) SEQUENCE DESCRIPTION: SEQ ID NO:26:

Lys Val Val Thr
1

(2) INFORMATION FOR SEQ ID NO:27:

(i) SEQUENCE CHARACTERISTICS:
      (A) LENGTH: 4 amino acids
      (B) TYPE: amino acid
      (C) STRANDEDNESS: single
      (D) TOPOLOGY: linear (i i) MOLECULE TYPE: peptide (x i) SEQUENCE DESCRIPTION: SEQ ID NO:27:

Phe Lys Val Val
1

(2) INFORMATION FOR SEQ ID NO:28:

(i) SEQUENCE CHARACTERISTICS:
      (A) LENGTH: 4 amino acids
      (B) TYPE: amino acid
      (C) STRANDEDNESS: single
      (D) TOPOLOGY: linear (i i) MOLECULE TYPE: peptide (x i) SEQUENCE DESCRIPTION: SEQ ID NO:28:

Gln Phe Lys Val
1

(2) INFORMATION FOR SEQ ID NO:29:

(i) SEQUENCE CHARACTERISTICS:
      (A) LENGTH: 4 amino acids
      (B) TYPE: amino acid
      (C) STRANDEDNESS: single
      (D) TOPOLOGY: linear (i i) MOLECULE TYPE: peptide (x i) SEQUENCE DESCRIPTION: SEQ ID NO:29:

Arg Gln Phe Lys
1

(2) INFORMATION FOR SEQ ID NO:30:

(i) SEQUENCE CHARACTERISTICS:
      (A) LENGTH: 4 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO:30:

Arg Arg Gln Phe
1

(2) INFORMATION FOR SEQ ID NO:31:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:31:

Leu Arg Arg Gln
1

(2) INFORMATION FOR SEQ ID NO:32:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:32:

Phe Leu Arg Arg
1

(2) INFORMATION FOR SEQ ID NO:33:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:33:

Pro Pro Pro Pro
1

(2) INFORMATION FOR SEQ ID NO:34:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:34:

Ala Ala Ala Ala
1

(2) INFORMATION FOR SEQ ID NO:35:

(i) SEQUENCE CHARACTERISTICS:
        (A) LENGTH: 4 amino acids
        (B) TYPE: amino acid
        (C) STRANDEDNESS: single
        (D) TOPOLOGY: linear (i i) MOLECULE TYPE: peptide (x i) SEQUENCE DESCRIPTION: SEQ ID NO:35:

Ala  Gly  Gly  Gly
            1

(2) INFORMATION FOR SEQ ID NO:36:

(i) SEQUENCE CHARACTERISTICS:
                (A) LENGTH: 4 amino acids
                (B) TYPE: amino acid
                (C) STRANDEDNESS: single
                (D) TOPOLOGY: linear (i i) MOLECULE TYPE: peptide (x i) SEQUENCE DESCRIPTION: SEQ ID NO:36:

Val  Val  Val  Val
            1

CYCLIC NUCLEIC ACID AND POLYPEPTIDE ARRAYS

CROSS REFERENCE TO RELATED APPLICATIONS

This is a Continuation of application Ser. No. 07/972,007 filed Nov. 5, 1992, now U.S. Pat. No. 5,527,681, which is a continuation-in-part of application Ser. No. 796,727, filed Nov. 22, 1991, now U.S. Pat. No. 5,242,974. This application is also a continuation-in-part of U.S. application Ser. No. 805,727, (now U.S. Pat. No. 5,424,186), filed Dec. 6, 1991, and priority is claimed from these applications. All of the above identified applications are incorporated herein by reference for all purposes.

U.S. application Ser. No. 805,727 is a continuation-in-part of U.S. application Ser. No. 624,120, filed Dec. 6, 1990 (abandoned) which is a continuation-in-part of U.S. application Ser. No. 492,462 (now U.S. Pat. No. 5,143,854), filed Mar. 7, 1990, which is a continuation-in-part of U.S. application Ser. No. 362,901, filed Jun. 7, 1989 (abandoned). No priority is claim from these applications.

This application is also related to the following United States applications: U.S. application Ser. Nos. 626,730 and 624,114, both filed Dec. 6, 1990; and U.S. application Ser. Nos. 796,243 and 796,947, both filed on Nov. 22, 1991, now U.S. Pat. Nos. 5,384,261 and 5,324,633, respectively. No priority is claimed from these applications and patents. Each of these applications is incorporated herein by reference for all purposes.

BACKGROUND OF THE INVENTION

The present invention relates to the field of molecular synthesis. More specifically, the invention provides systems and methods for directed synthesis of diverse molecular sequences on substrates.

Methods for preparing different polymers are well known. For example, the "Merrifield" method, described in Atherton et al., "Solid Phase Peptide Synthesis," IRL Press, 1989, which is incorporated herein by reference for all purposes, has been used to synthesize peptides on a solid support. In the Merrifield method, an amino acid is covalently bonded to a support made of an insoluble polymer or other material. Another amino acid with an alpha protecting group is reacted with the covalently bonded amino acid to form a dipeptide. After washing, the protecting group is removed and a third amino acid with an alpha protecting group is added to the dipeptide. This process is continued until a peptide of a desired length and sequence is obtained.

Other techniques have also been described. These methods include the synthesis of peptides on 96 plastic pins which fit the format of standard microtiter plates. Advanced techniques for synthesizing large numbers of molecules in an efficient manner have also been disclosed. Most notably, U.S. Pat. No. 5,143,854 (Pirrung et al.) and PCT Application No. 92/10092 disclose improved methods of molecular synthesis using light directed techniques. According to these methods, light is directed to selected regions of a substrate to remove protecting groups from the selected regions of the substrate. Thereafter, selected molecules are coupled to the substrate, followed by additional irradiation and coupling steps.

SUMMARY OF THE INVENTION

Methods, devices, and compositions for synthesis and use of diverse molecular sequences on a substrate are disclosed, as well as applications thereof.

A preferred embodiment of the invention provides for the synthesis of an array of polymers in which individual monomers in a lead polymer are systematically substituted with monomers from one or more basis sets of monomers. The method requires a limited number of masks and a limited number of processing steps. According to one specific aspect of the invention, a series of masking steps are conducted to first place the first monomer in the lead sequence on a substrate at a plurality of synthesis sites. The second monomer in the lead sequence is then added to the first monomer at a portion of the synthesis sites, while different monomers from a basis set are placed at discrete other synthesis sites. The process is repeated to produce all or a significant number of the mono substituted polymers based on the lead polymer using a given basis set of monomers. According to a preferred aspect of the invention, the technique uses light directed techniques, such as those described in Pirrung et al., U.S. Pat. No. 5,143,854.

Another aspect of the invention provides for efficient synthesis and screening of cyclic molecules. According to a preferred aspect of the invention, cyclic polymers are synthesized in an array in which the polymers are coupled to the substrate at different positions on the cyclic polymer ring. Therefore, a particular polymer may be presented in various "rotated" forms on the substrate for later screening. Again, the cyclic polymers are formed according to most preferred embodiments with the techniques of Pirrung et al.

The resulting substrates will have a variety of uses including, for example, screening polymers for biological activity. To screen for biological activity, the substrate is exposed to one or more receptors such as an antibody, oligonucleotide, whole cells, receptors on vesicles, lipids, or any one of a variety of other receptors. The receptors are preferably labeled with, for example, a fluorescent marker, a radioactive marker, or a labeled antibody reactive with the receptor. The location of the marker on the substrate is detected with, for example, photon detection or autoradiographic techniques. Through knowledge of the sequence of the material at the location where binding is detected, it is possible to quickly determine which polymer (s) are complementary with the receptor. The technique can be used to screen large numbers of peptides or other polymers quickly and economically.

A further understanding of the nature and advantages of the inventions herein may be realized by reference to the remaining portions of the specification and the attached drawings.

BRIEF DESCRIPTION OF THE DRAWINGS

FIGS. 7A to 7C illustrate formation of rotated and substituted cyclic polymers;

FIGS. 11A and 11B illustrate masks used in another embodiment;

FIGS. 13A to 13H illustrate donor/quencher pairs;

DESCRIPTION OF THE PREFERRED EMBODIMENTS

Contents

Figure 1A:
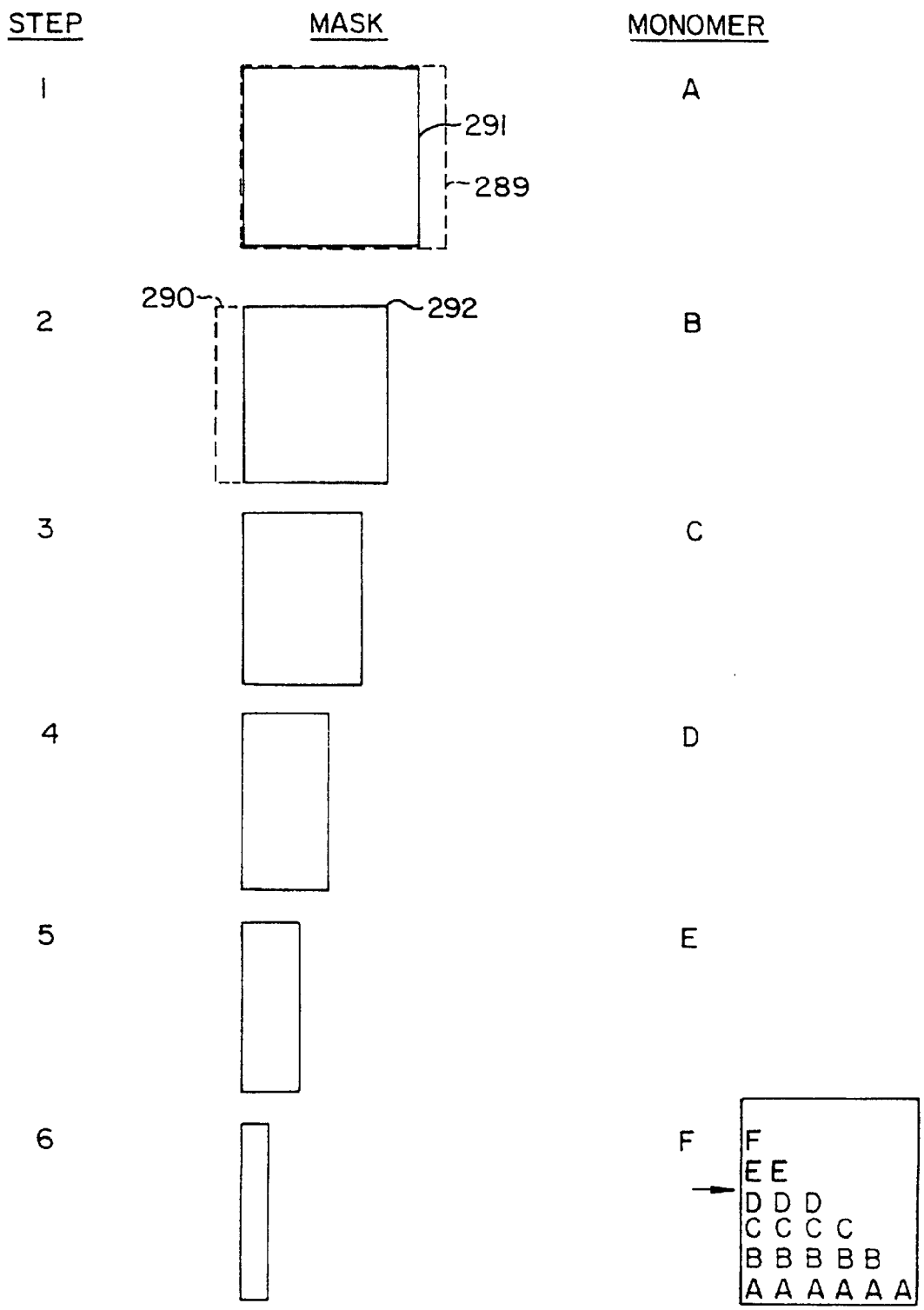
FIGS. 1A to 1C illustrate a systematic substitution masking strategy.

I. Definitions
II. Synthesis
   A. Systematic Substitution
   B. Cyclic Polymer Mapping
III. Data Collection
   A. CCD Data Collection System
   B. Trapping Low Affinity Interactions
   C. Fluorescence Energy-Transfer Substrate Assays
IV. Examples
   A. Example
   B. Example
V. Conclusion

I. Definitions

Certain terms used herein are intended to have the following general definitions:

1. Complementary: This term refers to the topological compatibility or matching together of interacting surfaces of a ligand molecule and its receptor. Thus, the receptor and its ligand can be described as complementary, and furthermore, the contact surface characteristics are complementary to each other.

2. Epitope: An epitope is that portion of an antigen molecule which is delineated by the area of interaction with the subclass of receptors known as antibodies.

3. Ligand: A ligand is a molecule that is recognized by a particular receptor. Examples of ligands that can be investigated by this invention include, but are not restricted to, agonists and antagonists for cell membrane receptors, toxins and venoms, viral epitopes, hormones, hormone receptors, peptides, enzymes, enzyme substrates, cofactors, drugs (e.g., opiates, steroids, etc.), lectins, sugars, oligonucleotides (such as in hybridization studies), nucleic acids, oligosaccharides, proteins, benzodiazapines, prostaglandins, beta-turn mimetics, and monoclonal antibodies.

4. Monomer: A monomer is a member of the set of smaller molecules which can be joined together to form a larger molecule. The set of monomers includes but is not restricted to, for example, the set of common L-amino acids, the set of D-amino acids, the set of natural or synthetic amino acids, the set of nucleotides and the set of pentoses and hexoses. As used herein, monomer refers to any member of a basis set for synthesis of a larger molecule. A selected set of monomers forms a basis set of monomers. For example, dimers of the 20 naturally occurring L-amino acids form a basis set of 400 monomers for synthesis of polypeptides. Different basis sets of monomers may be used in any of the successive steps in the synthesis of a polymer. Furthermore, each of the sets may include protected members which are modified after synthesis.

5. Peptide: A peptide is a polymer in which the monomers are natural or unnatural amino acids and which are joined together through amide bonds, alternatively referred to as a polypeptide. In the context of this specification, it should be appreciated that the amino acids may be, for example, the L-optical isomer or the D-optical isomer. Specific implementations of the present invention will result in the formation of peptides with two or more amino acid monomers, often 4 or more amino acids, often 5 or more amino acids, often 10 or more amino acids, often 15 or more amino acids, and often 20 or more amino acids. Standard abbreviations for amino acids are used (e.g., P for proline). These abbreviations are included in Stryer, *Biochemistry*, Third Ed., 1988, which is incorporated herein by reference for all purposes.

6. Radiation: Radiation is energy which may be selectively applied, including energy having a wavelength of between $10^{-14}$ and $10^4$ meters including, for example, electron beam radiation, gamma radiation, x-ray radiation, light such as ultra-violet light, visible light, and infrared light, microwave radiation, and radio waves. "Irradiation" refers to the application of radiation to a surface.

7. Receptor: A receptor is a molecule that has an affinity for a given ligand. Receptors may be naturally-occurring or synthetic molecules. Also, they can be employed in their unaltered state, in derivative forms, or as aggregates with other species. Receptors may be attached, covalently or noncovalently, to a binding member, either directly or via a specific binding substance. Examples of receptors which can be employed by this invention include, but are not restricted to, antibodies, cell membrane receptors, monoclonal antibodies and antisera reactive with specific antigenic determinants (such as on viruses, cells, or other materials), drugs, oligonucleotides, polynucleotides, nucleic acids, peptides, cofactors, lectins, sugars, polysaccharides, cells, cellular membranes, and organelles. Receptors are sometimes referred to in the art as anti-ligands. As the term receptors is used herein, no difference in meaning is intended. A "Ligand Receptor Pair" is formed when two molecules have combined through molecular recognition to form a complex.

Other examples of receptors which can be investigated by this invention include but are not restricted to microorganism receptors, enzymes, catalytic polypeptides, hormone receptors, and opiate receptors.

8. Substrate: A substrate is a material having a rigid or semi-rigid surface, generally insoluble in a solvent of interest such as water, porous and/or non-porous. In many embodiments, at least one surface of the substrate will be substantially flat, although in some embodiments it may be desirable to physically separate synthesis regions for different polymers with, for example, wells, raised regions, etched trenches, or the like. According to other embodiments, small beads may be provided on the surface which may be released upon completion of the synthesis.

9. Protecting group: A protecting group is a material which is chemically bound to a monomer unit or polymer and which may be removed upon selective exposure to an activator such as electromagnetic radiation or light, especially ultraviolet and visible light. Examples of protecting groups with utility herein include those comprising ortho-nitro benzyl derivatives, nitropiperonyl, pyrenylmethoxy-carbonyl, nitroveratryl, nitrobenzyl, dimethyl dimethoxybenzyl, 5-bromo-7-nitroindolinyl, o-hydroxy-α-methyl cinnamoyl, and 2-oxymethylene anthraquinone.

10. Predefined Region: A predefined region is a localized area on a surface which is, was, or is intended to be activated for formation of a molecule using the techniques described herein. The predefined region may have any convenient shape, e.g., circular, rectangular, elliptical, wedge-shaped, etc. For the sake of brevity herein, "predefined regions" are sometimes referred to simply as "regions." A predefined region may be illuminated in a specified step, along with other regions of a substrate.

11. Substantially Pure: A molecule is considered to be "substantially pure" within a predefined region of a substrate when it exhibits characteristics that distinguish it from other predefined regions. Typically, purity will be measured in terms of biological activity or function as a result of uniform sequence. Such characteristics will typically be measured by way of binding with a selected ligand or receptor. Preferably the region is sufficiently pure such that the predominant species in the predefined region is the desired sequence. According to preferred aspects of the invention, the molecules formed are 5% pure, more preferably more than 10% pure, preferably more than 20% pure, more preferably more than 80% pure, more preferably more than 90% pure, more preferably more than 95% pure, where purity for this purpose refers to the ratio of the number of ligand molecules formed in a predefined region having a desired sequence to the total number of molecules formed in the predefined region.

12. Activator: A activator is a material or energy source adapted to render a group active and which is directed from a source to at least a predefined location on a substrate, such as radiation. A primary illustration of an activator is light, such as visible, ultraviolet, or infrared light. Other examples of activators include ion beams, electric fields, magnetic fields, electron beams, x-ray, and the like.

13. Combinatorial Synthesis Strategy: A combinatorial synthesis strategy is an ordered strategy for parallel synthesis of diverse polymer sequences by sequential addition of reagents which may be represented by a reactant matrix and a switch matrix, the product of which is a product matrix. A reactant matrix is a 1 column by m row matrix of the building blocks to be added. The switch matrix is all or a subset of the binary numbers, preferably ordered, between 1 and m arranged in columns. A "binary strategy" is one in which at least two successive steps illuminate a portion, often half, of a region of interest on the substrate. In a binary synthesis strategy, all possible compounds which can be formed from an ordered set of reactants are formed. In most preferred embodiments, binary synthesis refers to a synthesis strategy which also factors a previous addition step. For example, a strategy in which a switch matrix for a masking strategy halves regions that were previously illuminated, illuminating about half of the previously illuminated region and protecting the remaining half (while also protecting about half of previously protected regions and illuminating about half of previously protected regions). It will be recognized that binary rounds may be interspersed with non-binary rounds and that only a portion of a substrate may be subjected to a binary scheme. A combinatorial "masking" strategy is a synthesis which uses light or other spatially selective deprotecting or activating agents to remove protecting groups from materials for addition of other materials such as amino acids.

14. Linker: A linker is a molecule or group of molecules attached to a substrate and spacing a synthesized polymer from the substrate for exposure/binding to a receptor.

15. Systematically Substituted: A position in a target molecule has been systematically substituted when the molecule is formed at a plurality of synthesis sites, with the molecule having a different member of a basis set of monomers at the selected position of the molecule within each of the synthesis sites on the substrate.

16. Abbreviations: The following frequently used abbreviations are intended to have the following meanings:
BOC: t-butyloxycarbonyl.
BOP: benzotriazol-1-yloxytris-(dimethylamino) phosphonium hexafluorophosphate.
DCC: dicyclohexylcarbodiimide.
DCM: dichloromethane; methylene chloride.
DDZ: dimethoxydimethylbenzyloxy.
DIEA: N,N-diisopropylethylamine.
DMAP: 4-dimethylaminopyridine.
DMF: dimethyl formamide.
DMT: dimethoxytrityl.
FMOC: fluorenylmethyloxycarbonyl.
HBTU: 2-(1H-benzotriazol-1-yl)-1,1,3,3-tetramethyluronium hexafluorophosphate.
HOBT: 1-hydroxybenzotriazole.
NBOC: 2-nitrobenzyloxycarbonyl.
NMP: N-methylpyrrolidone.
NPOC: 6-nitropiperonyloxycarbonyl.
NV: 6-nitroveratryl.
NVOC: 6-nitroveratryloxycarbonyl.
PG: protecting group.
TFA: trifluoracetic acid.
THF: tetrahydrofuran.

II. Synthesis

The present invention provides synthetic strategies and devices for the creation of large scale chemical diversity. Solid-phase chemistry, photolabile protecting groups, and photolithography are brought together to achieve light-directed spatially-addressable parallel chemical synthesis in preferred embodiments.

The invention is described herein for purposes of illustration primarily with regard to the preparation of peptides and nucleotides but could readily be applied in the preparation of other molecules. Such molecules include, for example, both linear and cyclic polymers of nucleic acids, polysaccharides, phospholipids, and peptides having either α-, β-, or ω-amino acids, heteropolymers in which a known drug is covalently bound to any of the above, polyurethanes, polyesters, polycarbonates, polyureas, n-alkylureas, polyamides, polyethyleneimines, polyarylene sulfides, polysiloxanes, polyimides, carbamates, sulfones, sulfoxides, polyacetates, or other polymers which will be apparent upon review of this disclosure. It will be recognized further that peptide illustrations herein are primarily with reference to C- to N-terminal synthesis, but the invention could readily be applied to N- to C-terminal synthesis without departing from the scope of the invention. Methods for forming cyclic and reversed polarity peptides and other polymers are described in copending application Ser. No. 796,727, filed Nov. 22, 1991, and previously incorporated herein by reference. Other molecules that are not conventionally viewed as polymers but which are formed from a basis set of monomers or building blocks may also be formed according to the invention herein.

The prepared substrate may, for example, be used in screening a variety of polymers as ligands for binding with a receptor, although it will be apparent that the invention could be used for the synthesis of a receptor for binding with a ligand. The substrate disclosed herein will have a wide variety of uses. Merely by way of example, the invention herein can be used in determining peptide and nucleic acid sequences that bind to proteins, finding sequence-specific binding drugs, identifying epitopes recognized by antibodies, and evaluating a variety of drugs for clinical and diagnostic applications, as well as combinations of the above.

The invention preferably provides for the use of a substrate "S" with a surface. Linker molecules "L" are optionally provided on a surface of the substrate. The purpose of the linker molecules, in some embodiments, is to facilitate receptor recognition of the synthesized polymers.

Optionally, the linker molecules are chemically protected for storage or synthesis purposes. A chemical protecting group such as t-BOC (t-butyloxycarbonyl) is used in some embodiments. Such chemical protecting groups would be chemically removed upon exposure to, for example, acidic solution and could serve, inter alia to protect the surface during storage and be removed prior to polymer preparation.

When a polymer sequence to be synthesized is, for example, a polypeptide, amino groups at the ends of linkers attached to a glass substrate are derivatized with, for example, nitroveratryloxycarbonyl (NVOC), a photoremovable protecting group. The linker molecules may be, for example, aryl acetylene, ethylene glycol oligomers containing from 2–10 monomers, diamines, diacids, amino acids, or combinations thereof.

According to one aspect of the invention, on the substrate or a distal end of the linker molecules, a functional group with a protecting group $P_0$ is provided. The protecting group $P_0$ may be removed upon exposure to an activator such as a chemical reagent, radiation, electric fields, electric currents, or other activators to expose the functional group. In a preferred embodiment, the radiation is ultraviolet (UV), infrared (IR), or visible light, or a basic or acidic reagent. In still further alternative embodiments, ion beams, electron beams, or the like may be used for deprotection.

Photodeprotection is effected by illumination of the substrate through, for example, a mask wherein the pattern produces illuminated regions with dimensions of, for example, less than 1 $cm^2$, $10^{-1}$ $cm^2$, $10^{-2}$ $cm^2$, $10^{-3}$ $cm^2$, $10^{-4}$ $cm^2$, $10^{-5}$ $cm^2$, $10^{-6}$ $cm^2$, $10^{-7}$ $cm^2$, $10^{-8}$ $cm^2$, or $10^{-10}$ $cm^2$. In a preferred embodiment, the regions are between about 10×10 $\mu$m and 500×500 $\mu$m. According to some embodiments, the masks are arranged to produce a checkerboard array of polymers, although any one of a variety of geometric configurations may be utilized.

Concurrently with or after exposure of a known region of the substrate to light or another activator, the surface is contacted with a first monomer unit $M_1$ which reacts with the functional group that has been exposed by the deprotection step. The first monomer includes a protecting group $P_1$. $P_1$ may or may not be the same as $P_0$.

Accordingly, after a first cycle, first regions of the surface comprise the sequence:

$$S\text{-}L\text{-}M_1\text{-}P_1$$

while remaining regions of the surface comprise the sequence:

$$S\text{-}L\text{-}P_0$$

Thereafter, one or more second regions of the surface (which may include all or part of the first region, as well as other regions) are exposed to light and contacted with a second monomer $M_2$ (which may or may not be the same as $M_1$) having a protecting group $P_2$. $P_2$ may or may not be the same as $P_0$ and $P_1$. After this second cycle, different regions of the substrate may comprise one or more of the following sequences:

$$S\text{-}L\text{-}M_1\text{-}M_2\text{-}P_2$$

$$S\text{-}L\text{-}M_2\text{-}P_2$$

$$S\text{-}L\text{-}M_1\text{-}P_1 \text{ and/or}$$

$$S\text{-}L\text{-}P_0$$

The above process is repeated until the substrate includes desired polymers of desired lengths. By controlling the locations of the substrate exposed to light and the reagents exposed to the substrate following exposure, one knows the location of each sequence.

According to some embodiments of the invention, multiple protecting groups are utilized. For example, when light-labile protecting groups are utilized to protect the growing polymer chain, it will be desirable in some embodiments to provide different protecting groups on at least selected side groups of the various monomers. For example, acid or base labile protecting groups may be particularly desirable when light labile protecting groups are used on the growing polymer chain. As a specific example, in the case of amino acids, the sulfhydryl groups of cysteine side chains can form disulfide bonds with one another. Accordingly, it will sometimes be desirable to protect such side groups with an acid or base labile protecting group, or a protecting group that is removed with a wavelength of light different from that which removes the protecting group on the growing polymer chain. Then, one can selectively couple these side chains by removing the appropriate protecting groups.

Thereafter, the protecting groups are removed from some or all of the substrate and the sequences are, optionally, capped with a capping unit C. The process results in a substrate having a surface with a plurality of polymers of the following general formula:

$$S\text{-}[L]\text{-}(M_i)\text{-}(M_j)\text{-}(M_k) \ldots (M_x)\text{-}[C]$$

where square brackets indicate optional groups, and $M_i \ldots M_x$ indicates any sequence of monomers. The number of monomers could cover a wide variety of values, but in a preferred embodiment they will range from 2 to 100.

In some embodiments, a plurality of locations on the substrate polymers contain a common monomer subsequence. For example, it may be desired to synthesize a sequence $S-M_1-M_2-M_3$ at first locations and a sequence $S-M_4-M_2-M_3$ at second locations. The process would commence with irradiation of the first locations followed by contacting with $M_1$-P, resulting in the sequence $S-M_1$-P at the first location. The second locations would then be irradiated and contacted with $M_4$-P, resulting in the sequence $S-M_4$-P at the second locations. Thereafter both the first and second locations would be irradiated and contacted with monomers $M_2$ and $M_3$ (or with the dimer $M_2-M_3$, resulting in the sequence $S-M_1-M_2-M_3$ at the first locations and $S-M_4-M_2-M_3$ at the second locations. Of course, common subsequences of any length could be utilized including those in a range of 2 or more monomers, such as 2 to 10 monomers, 2 to 20 monomers, or 2 to 100 monomers.

The polymers prepared on a substrate according to the above methods will have a variety of uses including, for example, screening for biological activity, i.e., such as ability to bind to a receptor. In such screening activities, the substrate containing the sequences is exposed to an unlabeled or labeled receptor such as an antibody, a receptor on a cell, a phospholipid vesicle, or any one of a variety of other receptors. In one preferred embodiment, the polymers are exposed to a first, unlabeled or labeled receptor of interest and thereafter exposed to a labeled receptor-specific recognition element, which is, for example, an antibody. This process can provide signal amplification in the detection stage.

The receptor molecules may or may not bind with one or more polymers on the substrate. The presence (or lack thereof) of the labeled receptor and, therefore, the presence of a sequence which binds with the receptor is detected in a preferred embodiment through the use of autoradiography, detection of fluorescence with a charge-coupled device, fluorescence microscopy, or the like. The sequence of the polymer at the locations where the receptor binding is detected may be used to determine all or part of a sequence which is complementary to the receptor.

Use of the invention herein is illustrated primarily with reference to screening for binding to a complementary receptor. The invention will, however, find many other uses. For example, the invention may be used in information storage (e.g., on optical disks), production of molecular electronic devices, production of stationary phases in separation sciences, production of dyes and brightening agents, photography, and in immobilization of cells, proteins, lectins, nucleic acids, polysaccharides, and the like in patterns on a surface via molecular recognition of specific polymer sequences. By synthesizing the same compound in adjacent, progressively differing concentrations., one can establish a gradient to control chemotaxis or to develop diagnostic "dipsticks," which, for example, titrate an antibody against an increasing amount of antigen. By synthesizing several catalyst molecules in close proximity, one can achieve more efficient multistep conversions by "coordinate immobilization." Coordinate immobilization also may be used for electron transfer systems, as well as to provide both structural integrity and other desirable properties to materials, such as lubrication, wetting, etc.

According to alternative embodiments, molecular biodistribution or pharmacokinetic properties may be examined. For example, to assess resistance to intestinal or serum proteases, polymers may be capped with a fluorescent tag and exposed to biological fluids of interest.

A high degree of miniaturization is possible, because the density of compounds on the surface is determined largely with regard to spatial addressability of the activator, in one case the diffraction of light. Each compound is physically accessible and its position is precisely known. Hence, the array is spatially-addressable, and its interactions with other molecules can be assessed.

According to one aspect of the invention, reactions take place in an appropriate reaction chamber that includes isolated fluid flow paths for heating or cooling liquids that are used to maintain the reaction chamber temperature at a desired level. In still further embodiments the reaction chamber is placed on a rotating "centrifuge" to reduce the volume of reactants needed for the various coupling/deprotection steps disclosed herein. In a centrifuge flow cell, the substrate is placed in the centrifuge such that, for example, when a monomer solution passes over the surface of the substrate a relatively thin film of the material is formed on the substrate due to the higher gravitational forces acting on the substrate. Accordingly, the volume of various reagents needed in the synthesis will be substantially reduced.

A. Systematic Substitution

According to one preferred embodiment of the invention, a "lead" sequence is identified using either the light directed techniques described herein, or more conventional methods such as those described in Geysen, *J. Imm. Methods* (1987) 102:259–274, incorporated herein by reference for all purposes, or through other knowledge of the structure of the receptor in question, such as through computer modeling information. As used herein, a "lead" or "kernel" sequence is a molecule having a monomer sequence which has been shown to exhibit at least limited binding affinity with a receptor or class of receptors.

Thereafter, a series of molecules related to the lead sequence are generated by systematic substitution, deletion, addition, or a combination of these processes at one or more positions of the molecule. A sequence with a binding affinity higher than the lead sequence can be (or may be) identified through evaluation of the molecules produced by these processes.

One aspect of the invention herein provides for improved methods for forming molecules with systematically substituted monomers or groups of monomers using a limited number of synthesis steps. Like the other embodiments of the invention described herein, this aspect of the invention has applicability not only to the evaluation of peptides, but also other molecules, such as oligonucleotides and polysaccharides. Light-directed techniques are utilized in preferred embodiments because of the significant savings in time, labor, and the like.

According to one aspect of the invention, a lead polymer sequence is identified using conventional techniques or the more sophisticated light directed techniques described herein. The lead sequence is generally represented herein by:

A B C D E F G where the various letters refer to amino acids or other monomers in their respective positions in the lead sequence. Although a polymer with seven monomers is used herein for the purpose of illustration, a larger or smaller number of monomers will typically be found in the lead polymer in most embodiments of the invention.

Using a selected basis set of monomers, such as twenty amino acids or four nucleotides, one generates the following series of systematically substituted polymers. The sequence of the molecules generated is determined with reference to the columns of the map. In other words, the "map" below can be viewed as a cross-section of the substrate:

```
G G G G G X

F F F F F X F

E E E E X E E

D D D X D D D

B X B B B B B

X A A A A A A
``` where X represents the monomers in a basis set of monomers such as twenty amino acids. For example, the twenty polymers XBCDEFG are generated within 20 individual synthesis sites on the substrate. In the case of 7-monomer lead peptides, the total number of peptides generated with all twenty monomers in the basis set is 140, i.e., 7 * 20, with 134 unique sequences being made and 7 occurences of the lead sequence.

One of the least efficient ways to form this array of polymers would be via conventional synthesis techniques, which would require about 938 coupling steps (134 peptides * 7 residues each). At the other extreme, each of these sequences could be made in 7 steps, but the sequences would be physically mixed, requiring separation after screening.

Figure 1B:
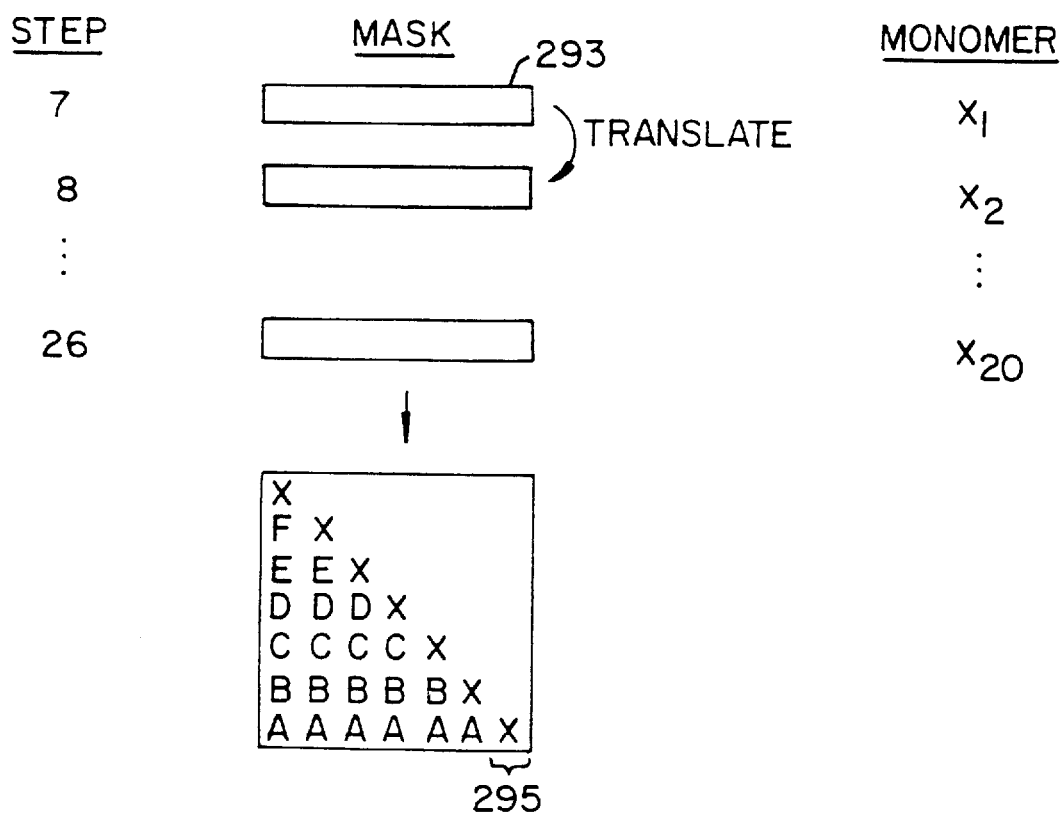
Figure 1C:
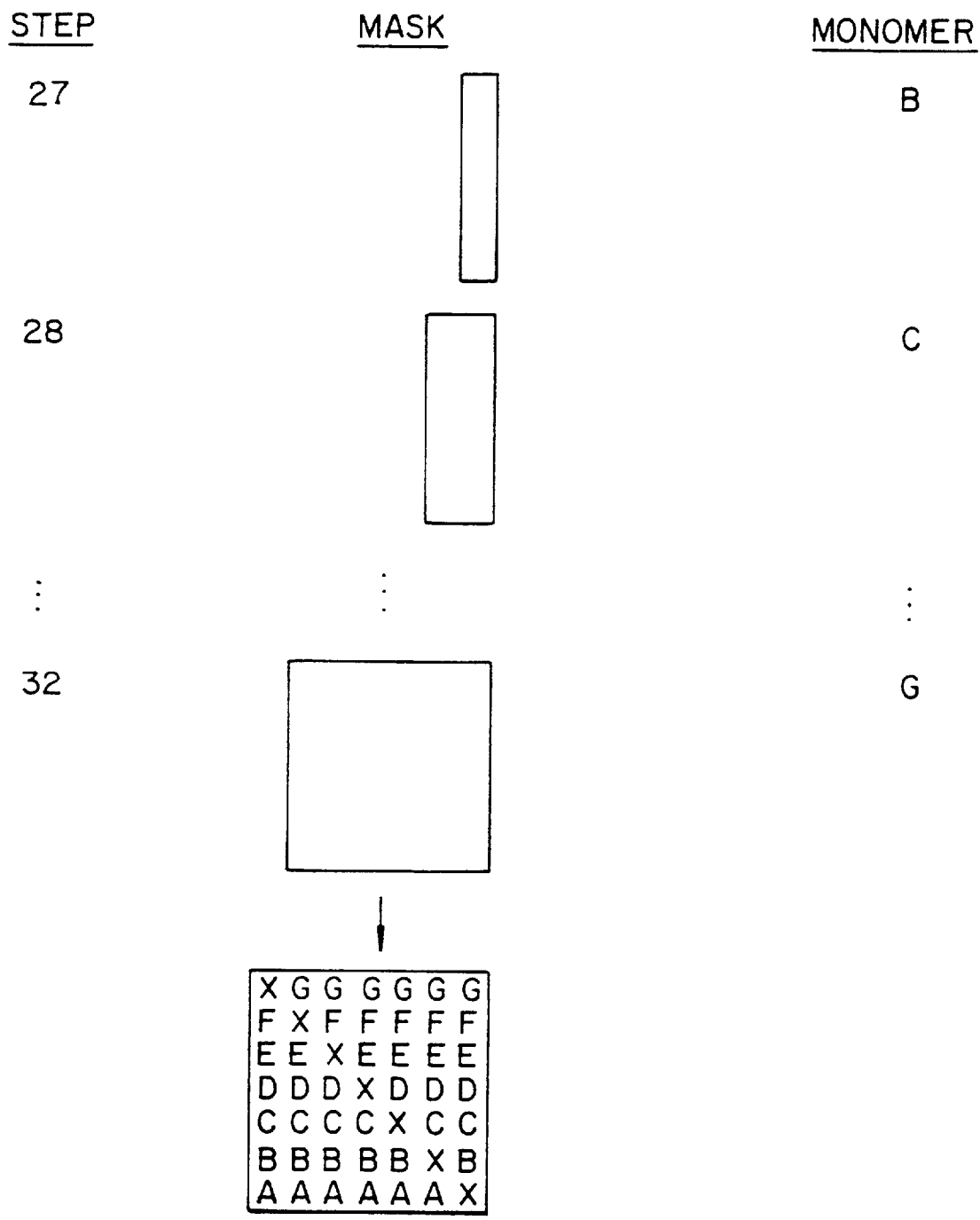

By contrast, this aspect of the invention provides for efficient synthesis of substituted polymers. FIGS. 1A–1C illustrates the masking strategy for the 7-monomer lead polymer. The particular masking strategy illustrated in FIGS. 1A–1C utilizes rectangular masks, but it will be apparent that other shapes of masks may also be used without departing from the scope of the invention herein. Masking techniques wherein regions of a substrate are selectively activated by light are described herein by way of a preferred embodiment. The inventions herein are not so limited, however, and other activation techniques may be utilized. For example, mechanical techniques of activation/coupling such as described in copending application Ser. No. 07/796,243 are used in some embodiments.

As shown in FIG. 1A, the process begins by exposing substantially all of a predefined region of the substrate to light with a mask 291, exposing approximately 6/7 of the region of interest 289. This step is followed by exposure of the substrate to monomer A. Thereafter, a mask 292 is used to expose approximately 5/7 of the region of interest, followed by coupling of B. It will be recognized that mask 292 may in fact be the same mask as 291 but translated across the substrate. Accordingly, regions indicated by dashed line 290, may also be exposed to light in this step, as well as in later steps. Thereafter, subsequent masking steps expose 4/7, 3/7, 2/7, and 1/7 of the area of interest on the substrate, each mask being used to couple a different monomer (C, D, E, F) to the substrate. The resulting substrate is schematically illustrated in the bottom portion of FIG. 1A along with the resulting polymer sequences thereon. Again, the composition of the sequences on the substrate is given by the vertical column such as "ABCDEF." As seen, 1- to 6-membered truncated portions of the target ABCDEFG are formed.

FIG. 1B illustrates the next series of masking steps. As shown in FIG. 1B, the same mask 293 is used for each masking step, but the mask is translated with respect to the substrate in each step. In each step, the mask illuminates a portion of each of the "stripes" of polymers formed in FIG. 1A, and in each step a different one of the monomers in a basis set is coupled to the substrate. The mask is then translated downwards for irradiation of the substrate and coupling of the next monomer. In the first step, the mask exposes the top 1/20 of each "stripe" of polymers shown in FIG. 1A, and monomer $X_1$ is coupled to this region. In the second step, the mask is translated downwards and $X_2$ is coupled, etc. The resulting substrate is shown in the bottom portion of FIG. 1B. An additional stripe 295 is formed adjacent the region addressed in FIG. 1A, this region containing a series of subregions, each containing one of the 20 monomers in this particular basis set.

Accordingly, after the steps shown in FIG. 1B, the substrate contains the following polymer sequences on the surface thereof (columns again indicating the sequences formed on the substrate):

```
                    X
                X   F
            X   E   E
        X   D   D   D
    X   C   C   C   C
X   B   B   B   B   B
X A A A A A A
``` where X indicates that an individual region contains one of each of the monomers in the basis set. Accordingly, for example, each of the 20 dimers AX are generated when the basis set is the 20 natural L-amino acids typically found in proteins. The 20 trimers of ABX, 4-mers of ABCX, etc., are also formed at predefined regions on the substrate.

Thereafter, as shown in FIG. 1C, the process continues, optionally using the same mask(s) used in FIG. 1A. The masks differ only in that they have been translated with respect to the substrate. In step 27, monomer B is added to the substrate using the mask that illuminates only the right 1/7 of the region of the substrate of interest. In step 28, the right 2/7 of the substrate is exposed and monomer C is coupled, etc. As shown in the bottom portion of FIG. 1C, the process results in the generation of all possible polymers based on the polymer ABCDEFG, wherein each monomer position is systematically substituted with all possible monomers from a basis set.

A number of variations of the above technique will be useful in some applications. For example, in some embodiments the process is varied slightly to form disubstitutions of a lead polymer in which the substitutions are in adjacent locations in the polymer. Such arrays are formed by one of a variety of techniques, but one simple technique provides for each of the masks illustrated in steps 7–26 of FIG. 1 to overlap the previous mask by some fraction, e.g., 1/3, of its height. According to such embodiments, the following array of polymers would be generated, in addition to the previous array of 134:

```
G G G G G X

F F F F F X X

E E E E X X F

D D D X X E E

B X X C C C C

X X B B B B B

X A A A A A A
```

The scheme may be expanded to produce tri-substituted, tetra-substituted, etc. molecules. Accordingly, the present invention provides a method of forming all molecules in which at least one location in the polymer is systematically substituted with all possible monomers from a basis set.

Figure 2:
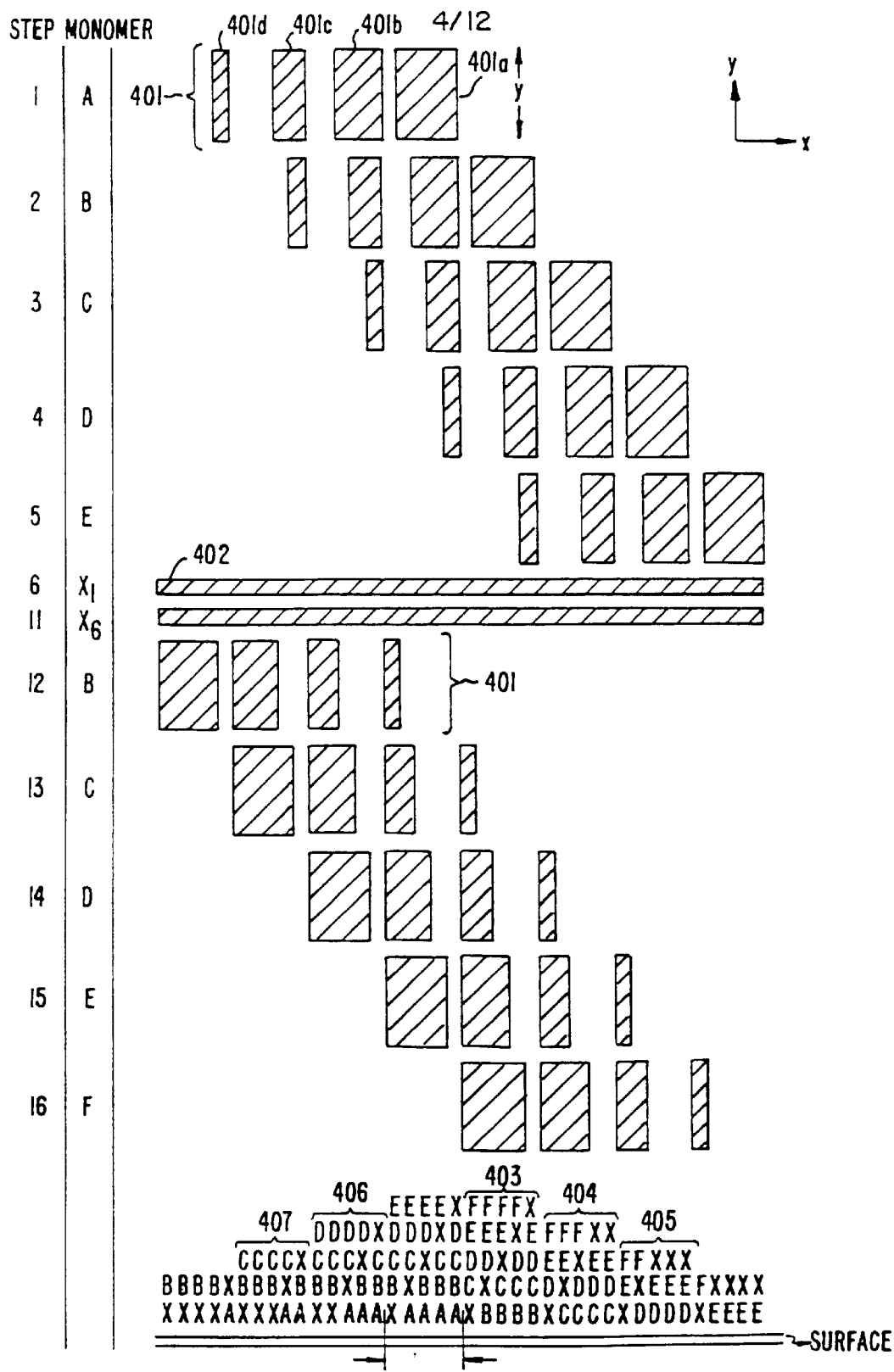
FIG. 2 illustrates additional aspects of a systematic substitution masking strategy.

According to a preferred aspect of the invention, masks are formed and reused to minimize the number of masks used in the process. FIG. 2 illustrates how masks may be designed in this manner. For simplicity, a 5-monomer synthesis is illustrated. The masks are illustrated from "above" in FIG. 2, with the cross hatching indicating light-transmissive regions. The resulting substrate is shown in the bottom portion of FIG. 2, with the region of primary interest for mono-substitutions indicated by the arrows.

FIG. 2 illustrates how to generate and systematically substitute all of the 5-mers contained in a 6-mer lead. A limited set of the possible 2-, 3-, and 4-mers is also synthesized. A 4-pattern mask was used. To make the 6-mers in a 7-mer kernel, a 5-pattern mask is used. To make the 7-mers in an 8-mer kernel, a 6-pattern mask is used, etc. To make all the 7-mers in a 12-mer kernel, a 6-pattern mask is still all that is needed. As a "bonus," all of the truncation sequences are generated with this strategy of letting the masks extend beyond the "desired" regions.

For example, FIG. 2 illustrates that in a 6-monomer sequence the 1- to 5-position substituted polymers are formed in the primary regions of interest (indicated by arrows), the 2- to 6-position substituted polymers are formed in region 403, the 3- to 6-position substituted polymers are formed in region 404, the 4- to 6-position substituted polymers in region 405, etc. The 1- to 4-position substituted polymers are formed in regions 406, the 1- to 3-position substituted polymers in region 407, etc.

In some embodiments, the substrate is only as large as the region indicated by arrows. It will often be desirable, however, to synthesize all of the molecules illustrated in FIG. 2 since the deletion sequences and others found outside of the region delineated by arrows will often provide additional valuable binding information.

As shown, a single mask 401 is used for all of steps 1–5, while another mask 402 is used for steps 6–11. The same mask 401 is used for steps 12–16, but the mask is rotated preferably 180 degrees with respect to the substrate. The light tranmissive regions of the mask 401 extend the full length ("Y") of the area of interest in the y-direction. As shown, in step 1, the mask is placed above the substrate, the substrate is exposed, and the A monomer is coupled to the substrate in selected portions of the substrate corresponding at least to the region 401a. Monomer A may also be placed at other locations on the substrate at positions corresponding to mask regions 401b, 401c, and 401d. Alternatively, these regions of the mask may simply illuminate regions that are off of the substrate or otherwise not of interest. If these regions correspond to regions of the substrate, various truncated analogs of the sequences will be formed.

Thereafter, as shown in step 2, the same mask is utilized, but it is translated to the right. The substrate is exposed by the mask, and the monomer B is then coupled to the substrate. Thereafter, coupling steps 3, 4, and 5 are conducted to couple monomers C, D and E, respectively. These steps also use the same mask translated to the right in the manner shown.

Thereafter, mask 402 is used for the "X" coupling steps. The mask 402 contains a single stripe that extends the full length ("X") of the area of interest in the x-direction. Mask 402 is preferably a single, linear stripe that will normally be of width Y divided by the number of monomers in the substitution basis set. For example, in the case of 6 amino acids as a basis set for the monosubstitution of peptides, the stripe will have a width of Y/6. The mask is repeatedly used to couple each of the monomers in the basis set of monomers and is translated downwards (or upwards) after each coupling step. For example, the mask may be placed at the top of the region of interest for the first coupling step, followed by translation downwards by ⅙ of the Y dimension for each successive coupling step when 6 monomers are to be substituted into the target. FIG. 2 shows only 2 mask steps for simplicity, but a greater number will normally be used.

Thereafter the mask 401 is again utilized for the remaining coupling steps. As shown, the mask 401 is rotated, preferably 180 degrees, for the following coupling steps. The succeeding coupling steps 12–16 are used to couple monomers B–F, respectively. The resulting substrate is shown in "cross section" in the bottom portion of FIG. 2. Again, the primary area of interest is designated by arrows and may be the only region used for synthesis on the substrate. The truncated substitutions outside of this region will also provide valuable information, however.

One extension of this method provides for the synthesis of all the possible double substitutions of a kernel sequence. For a kernel sequence 7 residues long, there are 8400 peptides that make up all possible disubstitutions of 20 amino acids, not considering replication (8380 unique). These peptides can be synthesized in 55 steps with 17 masks. The synthesized sequences are shown below:

G G G G G X G G G G X G G G X G G X G X X

F F F F X F F F F X F F F X F F X F X F X

E E E X E E E E X E E E X E E X E E X X E

D D X D D D D X D D D X D D D X X X D D D

X B B B B B X X X X X B B B B B B B B B B

X X X X X X A A A A A A A A A A A A A A A

The systematic substitution of three or more positions of the kernel sequence is also easily derived. The optimum polymer identified from the above strategy can then serve as the new kernel sequence in further iterations of this process. The present method may be used for any desired systematic substitution set, such as all 8-mers in a 12-mer kernel, substitution in cyclic polymers, and the like. This method provides a powerful technique for the optimization of ligands that bind to a molecular recognition element.

B. Cyclic Polymer Mapping

Copending application Ser. No. 07/796,727 (Entitled "Polymer Reversal on Solid Surfaces"), incorporated herein by reference for all purposes, discloses a method for forming cyclic polymers on a solid surface. According to one aspect of the present invention, improved strategies for forming systematically varied cyclic polymers are provided.

In the discussion below, "P" refers to a protecting group, and X, Y, and Z refer to the various reactive sites on a tether molecule T. A, B, C, D, E, and F refer to various monomers or groups of monomers. To synthesize a cyclic polymer according to one aspect of the invention herein, the process is conducted on a substrate. A tether molecule T is coupled to a surface of the substrate. T may be one of the monomers in the polymer, such as glutamic acid in the case of amino acids. Other examples of amino acid tether molecules include, but are not limited to, serine, threonine, cysteine, aspartic acid, glutamic acid, tyrosine, 4-hydroxyproline, homocysteine, cysteinesulfinic acid, homoserine, ornithine, and the like. The tether molecule includes one or more reactive sites such as a reactive site Z which is used to couple the tether to the substrate. The tether also includes a reactive site X having a protecting group $P_2$ thereon. The tether molecule further includes a reactive site Y with a protecting group $P_1$ thereon.

In a first step, a polymer synthesis is carried out on the reactive site Y. According to some embodiments, conventional polymer synthesis techniques are utilized such as those described in Atherton et al., previously incorporated herein by reference for all purposes. A wide variety of techniques may be used in alternative embodiments. For example, according to one embodiment, a variety of polymers with different monomer sequences are synthesized on the substrate. Such techniques may involve the sequential addition of monomers or groups of monomers on the growing polymer chain, each monomer of which may also have a reactive site protected by a protecting group.

A variety of such methods are available for synthesizing different polymers on a surface. For example, Geysen et al., "Strategies for Epitope Analysis Using Peptide Synthesis," *J. Imm. Meth.*, (1987) 102:259–274, incorporated herein by reference for all purposes, describes one commonly used technique for synthesizing different peptides using a "pin" technique. Other techniques include those of Houghten et al., *Nature* (1991) 354:84–86, incorporated herein by reference. In some embodiments, advanced techniques for synthesizing polymer arrays are utilized, such as those described in copending application Ser. No. 07/796,243, or light-directed, spatially-addressable techniques disclosed in Pirrung et al., U.S. Pat. No. 5,143,854; U.S. application Ser. No. 07/624,120; and Fodor et al., "Light-Directed Spatially-Addressable Parallel Chemical Synthesis," *Science* (1991) 251:767–773, all incorporated herein by reference for all purposes, such techniques being referred to herein for purposes of brevity as VLSIPS™ (Very Large Scale Immobilized Polymer Synthesis) techniques.

During polymer synthesis, the activator used to remove $P_1$ (if any) on the Y reactive site, and on reactive sites of the growing polymer chain, should be different than the activator used to remove the X protecting group $P_2$. Merely by way of example, the activator used to remove $P_2$ may be a first chemical reagent, while the activator used to remove the protecting group $P_1$, may be a second, different chemical reagent such as acid or base. By way of further example, the activator used to remove one of the protecting groups may be light, while the activator used to remove the other protecting group may be a chemical reagent, or both activators may be light, but of different wavelengths. Of course, other combinations will be readily apparent to those of skill in the art on review of this disclosure.

By virtue of proper protecting group selection and exposure to only the $P_1$ activator, the reactive site X is protected during polymer synthesis and does not take part in the initial portion of the process. Also, the reactive site Y remains bound to the monomer A. The synthesis step of the process, which will frequently include many substeps of deprotection/coupling, results in a polymer of a desired length, such as ABCD . . . F. A polymer with 5 or more monomers is used by way of example, but fewer (or more) monomers will be utilized according to some embodiments.

In a next step of the process, the protecting group $P_2$ on the X reactive site is removed. In addition, the reactive site on the last monomer F is rendered active, if necessary. The reactive site on the selected monomer will then react with the reactive site X, forming a cyclic polymer. In a preferred embodiment for peptide synthesis, the protecting group $P_2$ is removed with light.

Choice of the various protecting groups will generally be dictated by the type of polymer which is to be synthesized and the desired synthesis technique. Therefore, for example, oligonucleotides will often have different protecting groups than will peptides, oligosaccharides, and the like. In addition, conventional solid-phase synthesis techniques without the use of photoremovable protecting groups will utilize different protecting groups than VLSIPS™ light-directed synthesis techniques. Specific examples of protecting groups are discussed in detail below. Table 1 summarizes the various protecting groups used according to most preferred embodiments of the invention.

TABLE 1

Preferred Protecing Group Selections

| Synthesis | $P_1$/ Activator | $P_2$/ Activator |
|---|---|---|
| Standard Peptide | FMOC/Base | NVOC or other photochemical/ base or light |
| Standard Peptide | BOC/Acid | NVOC or other photochemical/ base or light |
| Standard Nucleotide | DMT/ Mild Acid | NVOC or other photochemical/ light |
| VLSIPS ™ Peptide | NVOC (or other photo- chemical protecting groups)/ Light | FMOC, allyl, silyl, or other base sens./base |
| VLSIPS ™ Nucleotide | NV or NVOC/ Light | DMT or other acid sens./acid |

One technique of standard Merrifield peptide synthesis employs fluorenylmethyloxycarbonyl (FMOC) on the growing end (amino terminus) of the polymer and one or more of a variety of side chain protecting groups. According to preferred embodiments herein, such techniques generally utilize mild base treatment to remove the FMOC ($P_1$) for peptides and strong acid (up to 100% TFA) for both removal of the side chain protecting groups and cleavage of the tether/ polymer bond. Base or light is used to remove the protecting group $P_2$, which may be, for example, NVOC.

One embodiment of the invention utilizes a group Pi which is removable with a first wavelength of light and a second photocleavable group $P_2$ which requires a different wavelength for deprotection of X. Preferably such groups utilize wavelengths >300 nm to avoid conflicting with protecting groups in use during polymer synthesis and to avoid damage to sensitive amino acids. Alternatively, some embodiments employ a base-, palladium- or fluoride-sensitive protecting group. Other such materials include FMOC, β cyanoethyl, t-butyldiphenylsilyl, allyl and others apparent to those of skill in the art.

Cyclic polymers immobilized on a surface present unique opportunities for biological activity screening. For example, with a cyclic polymer it is desirable to vary not only the monomers in the polymer, but also the point at which the cyclic polymer attaches to the substrate and, therefore, the region of the polymer available for binding. Further, depending on the building blocks of the polymer, one or more of the building blocks may not be amenable to attachment to a substrate.

Figure 3:
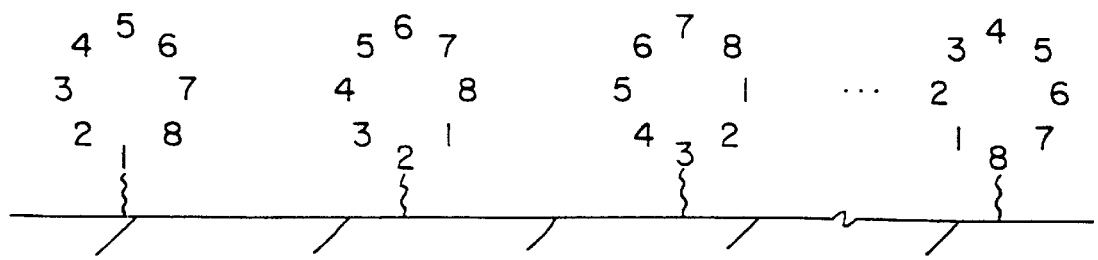
FIGS. 3, 4, and 5 illustrate rotated cyclic polymer groups.

FIG. 3 illustrates this aspect of the invention. In the particular embodiment shown in FIG. 3, a cyclic polymer made from 8 monomers is illustrated. As shown therein, it is desirable to synthesize the polymer so that it is attached to the substrate at different positions in the ring. For example, the left-most molecule in FIG. 3 is attached to the substrate with monomer 1, the second polymer is synthesized such that it is attached to the substrate via monomer 2, and the third polymer is attached to the substrate via monomer 3. In the most general case, it is desirable to synthesize an array of cyclic polymers in which a polymer is attached to the substrate via each of the monomer positions. For example, with reference to FIG. 3, it is desirable to attach the 8-monomer polymer via each of the 8 monomers therein. The site available for recognition will be slightly different for the polymer for each attachment position, because the polymer is presented in a "rotated" position on the various regions of the substrate.

Again, while the invention is illustrated with regard to cyclic polymers with about 8 monomers, a wide range of polymers may be utilized in conjunction with the invention without departing from the scope thereof. For example, when the polymers are peptides, the polymer molecules will typically contain between about 4 and 10 monomers, often between about 6 and 8 monomers.

Difficulties arise, however, in the attachment of certain monomers to the substrate. For example, in the case of amino acids, certain amino acids do not have side groups that are amenable to attachment to a solid substrate. Accordingly, in one embodiment of the invention, an array of cyclic polymers is synthesized in which the monomer used for attachment to the substrate is readily attachable to the substrate, such as glutamic acid. Like the first embodiment, the polymers have a common monomer sequence. However, the monomer used for coupling in all of the sites, according to this embodiment, is a common monomer that is easily coupled to the substrate.

Figure 4:
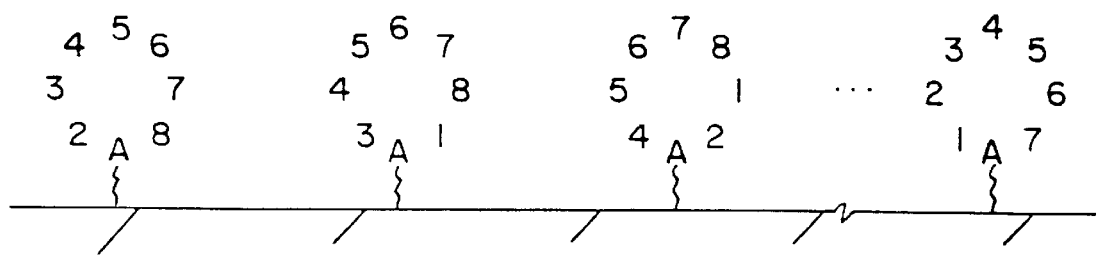
Figure 5:
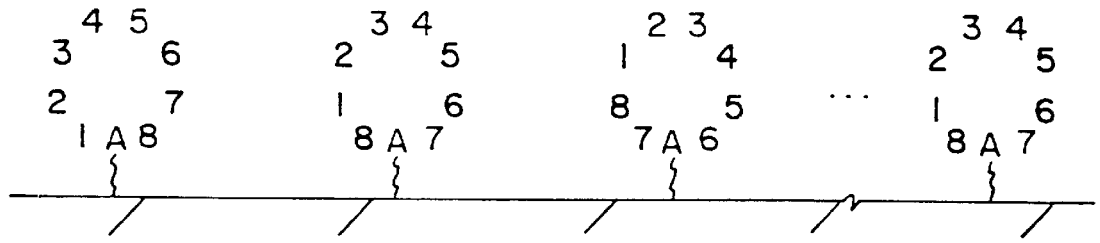

The substrate attachable monomer may either be substituted into the native polymer sequence at various locations by alternatively deleting one member of the polymer chain or by inserting the substrate attachable monomer into the native polymer sequence at different locations. FIGS. 4 and 5 illustrate these alternatives, with FIG. 4 illustrating a substitution strategy (in which a selected tether molecule is substituted into the native ring at the coupling site), and FIG. 5 illustrating an insertion strategy (in which a selected tether molecule is added to the native ring at the coupling site).

As shown in FIG. 4, substrate attachable monomer "A," referred to elsewhere herein as a tether, is coupled to the substrate and links the cyclic polymer to the substrate. In preferred embodiments, A substitutes for the monomer that would otherwise be in the position of the polymer that is coupled to the substrate. This substitution preserves the original ring size. For example, in the cyclic polymer molecule in the left portion of FIG. 4, the monomer A has been substituted for the monomer 1. The monomer A has been substituted for the monomer 2 in the polymer in the second portion of FIG. 4. The monomer A has been substituted for the monomer 3 in the polymer in the next polymer of FIG. 4.

In most embodiments, it will be desirable to synthesize an array of cyclic polymers in which the polymers are coupled to the substrate at each monomer position in the polymer. For example, in the case of an 8-mer, there will be 8 different attachment positions for the polymer. Often, it will be desirable to synthesize arrays of polymers simultaneously in which not only is the attachment position varied for an individual monomer, but different polymer molecules are formed on the substrate. For example, in the case of a cyclic pentapeptide with all possible combinations of natural amino acid monomers and all possible attachment positions, it may be desirable to synthesize all 800,000 combinations of sequence and attachment locations on one or more substrates.

According to a preferred aspect of the invention, a single mask may be used to form cyclic polymers with varying points of attachment on a substrate. FIGS. 6A to 6E illustrate one preferred masking strategy, using a 7-monomer cyclic polymer as an example. Formation of the rotated cyclic polymers on the same substrate with formation of polymers having different monomers at the various positions of the polymers represents a preferred embodiment of this invention. Only those steps relevant to the formation of rotated cyclic polymers are outlined below for the purpose of simplicity in the illustration.

Figure 6A:
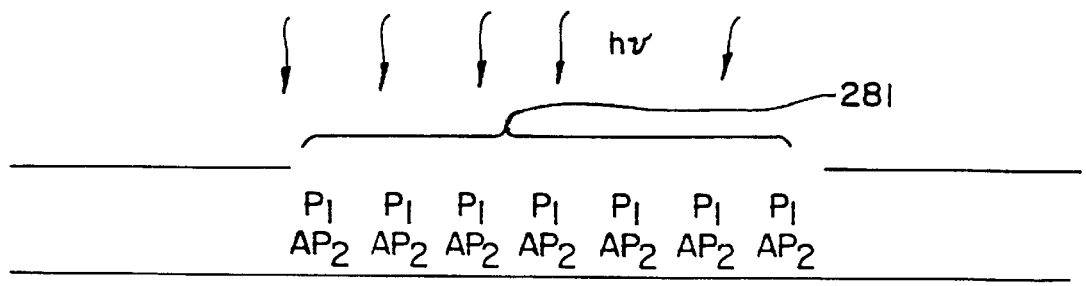
FIGS. 6A to 6E illustrate formation of rotated cyclic polymers.

As shown in FIG. 6A, the process begins with the illumination and coupling of molecule A to the surface in a region of interest 281. Molecule A may be attached directly or indirectly (via linkers) to the solid substrate. Molecule A is provided with terminal protecting group $P_1$ and side protecting group $P_2$ if necessary. $P_1$ and $P_2$ are removable under different conditions. For example, in a preferred embodiment of the invention $P_1$ is removable upon exposure to light and $P_2$ is removable upon exposure to, for example, acid or base. Details of various tether molecules A and protecting groups are included in copending application Ser. No. 07/796,727, previously incorporated herein by reference.

Figure 6B:
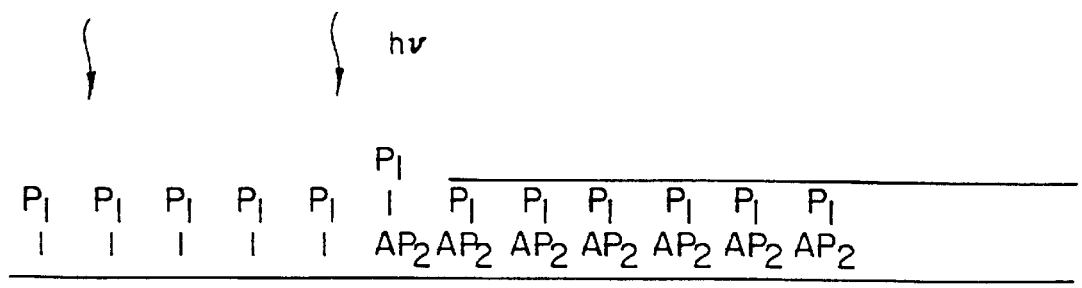

Thereafter, as shown in FIG. 6B, the mask is translated so as to expose only the left-most portion of the region of interest, and monomer 1 is coupled to the substrate. Monomer 1 also has a photoprotecting group on a terminus thereof. As shown, monomer 1 may also be coupled on areas of the substrate that are not in the region of interest, or the region to the left of the region of interest may be off of the edge of the substrate. The left and right portions of the substrate will, accordingly, be ignored in the illustrations below.

Figure 6C:
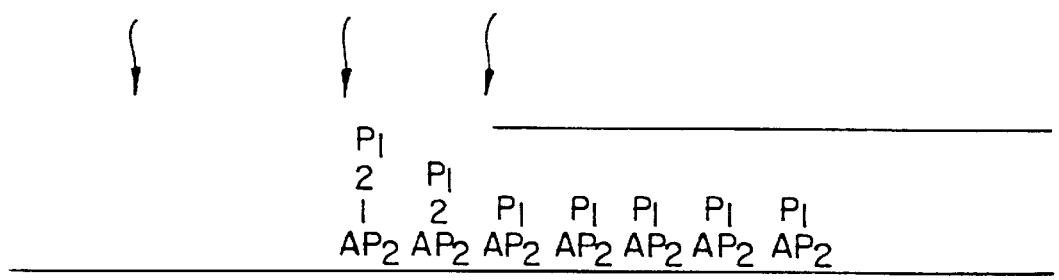
Figure 6D:
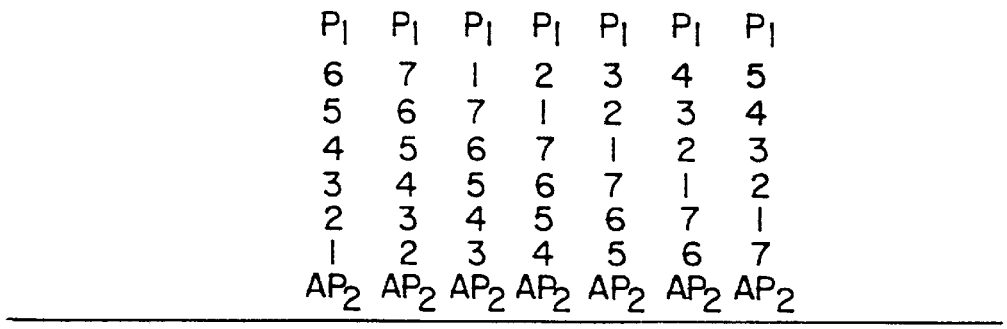

Thereafter, the process continues as illustrated in FIG. 6C, in which monomer 2 is coupled to the growing polymer chain using the same mask, again translated by one position. Processing continues with successive exposures to light using the translated mask, followed by coupling of the appropriate monomers, resulting in the substrate shown in FIG. 6D. Thereafter, the photoprotecting groups are removed from the terminus of all of the terminal monomers.

Figure 6E:
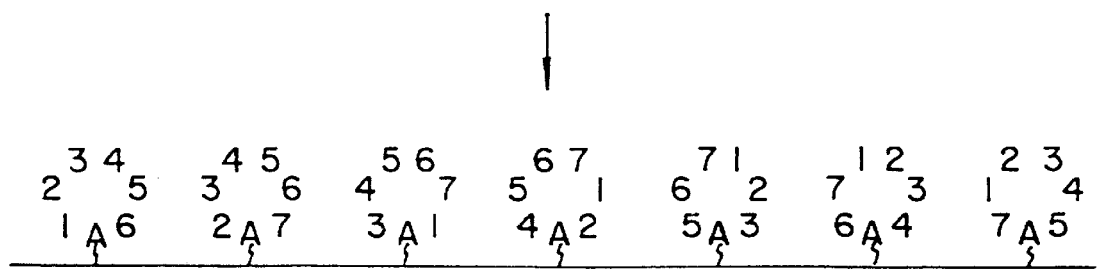

Then, the side chain protecting groups are removed from each of the tether molecules A, followed by coupling of the terminal monomers to the formerly protected side chain groups, in accordance with the teachings of Ser. No. 07/796,727. Accordingly, an array of polymers is produced as shown in FIG. 6E that contains spatially addressable regions containing the cyclic 7 member polymer, each coupled at a different position in the polymer via a common tether molecule.

In some embodiments it may be desirable to identify a target cyclic polymer, and synthesize an array of cyclic polymers in which not only is the polymer rotated, but also in which the monomers are systematically substituted with various monomers from a basis set. For example, it may be desirable to synthesize all polymers in which the 6th building block is systematically substituted with 20 L-amino acids.

In accordance with this aspect of the invention, an "X" mask is included in the synthesis strategy, similar to the method described above for linear polymers. The X mask is used to couple each of the monomers from a basis set in a selected position of the cyclic polymer. Accordingly, the resulting array in preferred embodiments contains all of the polymers in which one position is systematically varied. In addition, for each polymer, the polymer is coupled via each position in the monomer to the substrate.

For purposes of illustration, a cyclic polymer of 7 residues is shown. FIGS. 7A to 7C illustrate one preferred masking strategy for forming such cyclic polymer arrays. The particular embodiment shown in FIG. 7 illustrates substitution of monomers at the "6" position. As shown in FIG. 7A, processing of the substrate is initially the same as that shown in FIG. 6, in which the A tether as well as monomers 1–5 are coupled to the substrate. As shown in FIG. 7B (top view), the substrate is then processed with an "X" mask. The X mask is used to couple the various monomers from a basis set to the substrate. The X mask may be the same for coupling of each member of the basis set and is simply translated for the coupling. For example, in the first exposure, the X mask is arranged in the form of a horizontal rectangle at the top of the region of interest on the substrate, and the first monomer from the basis set ($X_1$) is coupled in this region. The X mask traverses each of the regions shown in FIG. 7A. The mask is then translated downwards, and the second monomer in the basis set ($X_2$) is coupled in this region, again with the mask traversing each of the regions formed up to the step shown in FIG. 7A. The mask is translated successively downwards until, for example, all 20 monomers in the basis set are coupled at various regions of the substrate, as indicated in FIG. 7B.

Thereafter, the original mask is again utilized. The mask is first used to couple monomer 7 to the right ⅚ of the substrate shown in FIG. 7B. The mask is then translated and used to couple monomer 1 to the right ⅘ of the substrate shown in FIG. 7B. The mask is then used to couple monomer 2 to the right ⅗ of the substrate shown in FIG. 7B. Successive couplings are conducted with monomers 3, 4, and 5. The sequences of monomers on the resulting substrate are illustrated below, where X indicates that a region of the substrate contains polymers with each of the basis set of monomers selected for insertion at the 6th position of the polymer. The polymer sequences are obtained by examination of the columns of the illustration below:

```
    X 7 1 2 3 4
    5 X 7 1 2 3
    4 5 X 7 1 2
    3 4 5 X 7 1
    2 3 4 5 X 7
    1 2 3 4 5 X
    A A A A A A
```

Thereafter, the polymers are cyclized, resulting in an array of polymers in which every member of the basis set is inserted at the sixth position of the polymers, and in which each polymer thus synthesized is coupled to the substrate at each rotational position in the polymer, all at spatially addressable regions. A portion of the resulting array is illustrated in FIG. 7C.

To vary every building block at every position systematically requires a different set of masks. For the above 7-numbered cyclic peptide, the length of the synthesis region is divided into 36 equal units, while the width of the synthesis region is divided into "x" units (typically x=20 for peptides with "natural" amino acids). The resulting polymer library will be as follows, again with columns indicating the resulting polymer sequence and "X" indicating that polymers with all members of a basis set substituted at that position are formed:

```
66666X11111X22222X33333X44444X55555X

5555X56666X61111X12222X23333X34444X4

444X44555X55666X66111X11222X22333X33

33X33344X44455X55566X66611X11122X222

2X22223X33334X44445X55556X66661X1111

X11111X22222X33333X44444X55555X66666

AAAAAAAAAAAAAAAAAAAAAAAAAAAAAAAAAAAA
```

Figure 8:
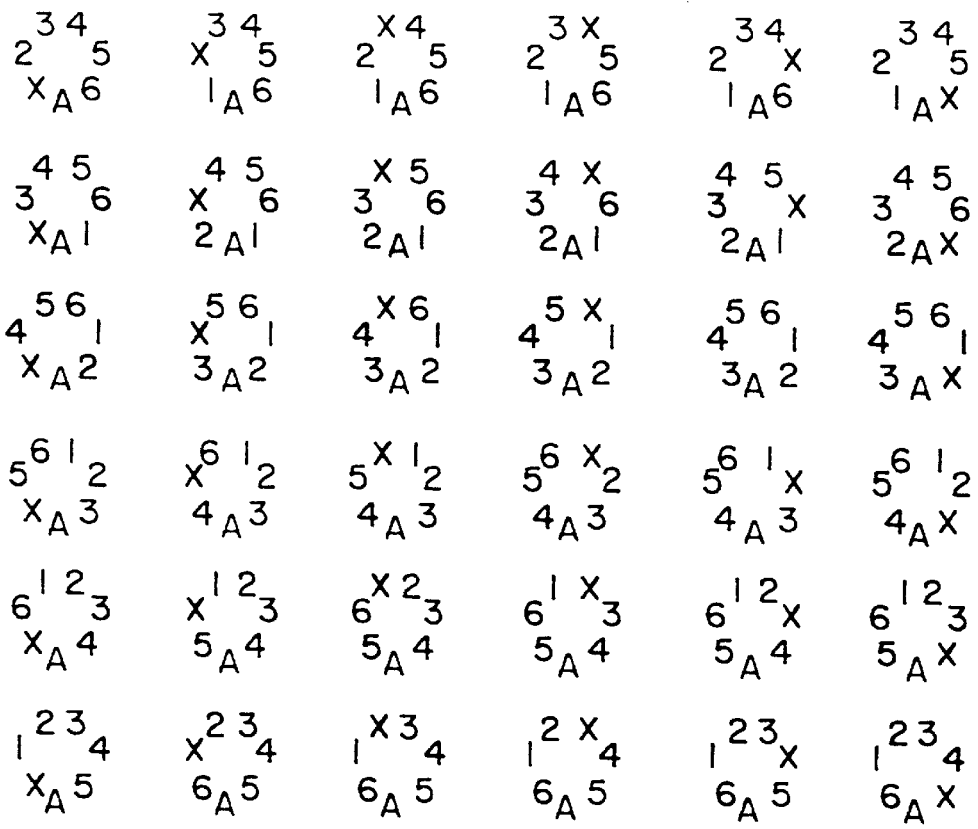
FIG. 8 illustrates the array of cyclic polymers resulting from the synthesis.
Figure 9:
FIG. 9 illustrates masks used in the synthesis of cyclic polymer arrays.

In synthesizing the above polymers, the order of coupling will be: A1234561234X2345612345. FIG. 8 illustrates the cyclic polymers resulting from the synthesis. FIG. 9 illustrates a convenient mask used in the synthesis.

Figure 10A:
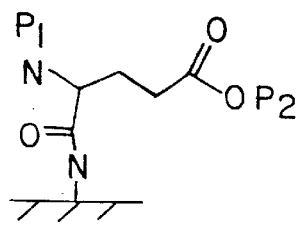
FIGS. 10A and 10B illustrate coupling of a tether in two orientations.
Figure 10B:
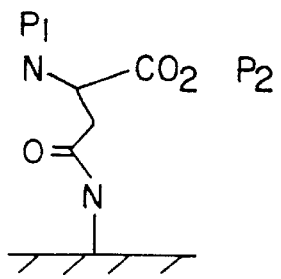

This strategy differs slightly from those discussed above in that the synthesis produces 7-membered rings in which the tether polymer is added to 6-membered kernel sequence. To mimic the structure of the actual polymer more closely, it is desirable in some embodiments to use a tether molecule that is shorter than the monomer molecules so as to maintain the native length of the molecule. For example, in the case of peptides, a disulfide molecule serving as the tether will be beneficial. Examples of such cyclic peptides with a disulfide linkage are common in the literature, i.e., oxytocin and vasopressin. The 6 amino acids and the disulfide linkage will produce a 20-membered ring. By comparison, a cyclic hexamer of a peptide is an 18-membered ring, while a cyclic peptide heptamer will be a 21-membered ring. Accordingly, when the disulfide molecule is inserted into the cyclic polymer, the tether will produce polymers that more correctly mimic the native polymer. Other useful tether molecules include glutamic acid, as illustrated in FIGS. 10A and 10B.

The following series of polymers can be made with the same masks (one to lay down "A", two with 180° symmetry to assemble the polymer, and one "X" mask). This method produces all single substitutions possible while maintaining the rest of the cycle constant. One could also use the method to make double and triple substitutions.

```
77777X11111X22222X33333X44444X55555X66666X

6666X67777X71111X12222X23333X34444X45555X5

555X55666X66777X77111X11222X22333X33444X44

44X44455X55566X66677X77711X11122X22233X333

3X33334X44445X55556X66667X77771X11112X2222

X22222X33333X44444X55555X66666X77777X11111

AAAAAAAAAAAAAAAAAAAAAAAAAAAAAAAAAAAA
    AAAA
```

In the above set of polymers A is the molecule used to couple the polymer to the substrate, 1–7 are amino acids or other monomers in the kernel sequence, and X are the substitutions from the basis set of monomers. One way to assemble this array is: A23456712345X34567123456. The masks that would be utilized before the X coupling are shown in FIG. 11A, and the masks used after the X coupling are shown in FIG. 11B.

III. Data Collection

A. CCD Data Collection System

Although confocal detection systems are typically used for data collection, according to one embodiment a high resolution CCD camera system is utilized for data collection. The camera allows for the digitization of images with a resolution of, e.g., 1300 by 1024 pixels. A dynamic range of >60 dB can be obtained if the sensor is calibrated with respect to dark current and gain. Cooling the camera to 248° K lowers the dark current to a tolerable level even when prolonged exposure times (several minutes) are needed.

According to one embodiment, a 100 W Hg-Arc lamp is used as a light source. The infrared components of the light are blocked using a heat-absorbing filter. A second filter is used to select the excitation wavelength using an optional ground glass plate filter. Best results are achieved by illuminating the sample with UV. Although the optimum excitation wavelength for FITC lies at 490 nm, excitation in the UV range shows better results than with a 490 nm IF filter, because the Hg lamp provides more optical energy in the UV band. The sample is illuminated at an angle of 45° with respect to the light beam and the CCD camera. This ensures that no direct light path exists between the lamp and the sensor and therefore reduces background radiation.

The CCD camera is mounted at the back of a Hasselblad 500 C/M camera system with a lens and IR filter. An automatic bellow and a standard 80 mm (f 2.8) lens are used. This system results in an imaging scale which is selectable between 1:3 and 1:0.8. The sample plus the filters are housed in a case to prevent light from the surroundings from entering the optical path. Digitized image data are transmitted to a 386 PC, where the images can be viewed on a high resolution display.

Longer integration times (up to 2 minutes) yield better S/N ratios. One problem is the fluorescence (and light diffraction) of dust particles on the surface of the chip used for the Very large Scale Immobilize Polymer Synthesis (VLSIPS™) techniques. Dust particles deliver a signal about 10 times higher than the FITC fluorescence. Therefore, the integration time can be increased only as long as the dust particles do not cause an overflow (blooming) of the sensor. However, since an area of about 50×50 pixels can be averaged in the digitized image for a quantitative assessment of the fluorescence, the measurement accuracy is sufficient with integration times between 15 and 30 seconds.

If the acquisition time needs to be lower than the 15–20 seconds mentioned above, a different light source should be selected. An argon ($\lambda$=488 nm) laser is optimal. The disadvantage of using a laser is the considerably higher technological expense, and the possibility of bleaching if the optical energy is raised too much. Bleaching could not be observed while using the Hg lamp (even with integration times of several minutes). Using a lens with a lower focal length (e.g., a standard 50 mm/f 1.4 lens) would improve the overall efficiency of the system.

The optimized optical system could allow for measurement times below 10 seconds using a Hg lamp. When using a laser, image acquisition will take less than 1 second. The system should be operated in a dust-free environment (such as a lateral flow workbench) to reduce errors generated by dust particles.

B. Trapping Low Affinity Interactions

According to one embodiment, the invention provides a methodology for chemically trapping-low affinity interactions between receptors and immobilized ligands. Monovalent receptors with $K_d$'s greater than 100 nM may not bind with sufficient affinity to an immobilized ligand to survive subsequent washing and imaging steps for later detection. Thus, while high concentrations (approximately near the $K_d$ of the peptide lead) of receptor should bind to some epitopes on, for example, a VLSIPS™ chip, this information may be lost during subsequent processing. Accordingly, cross-linkers are used according to one embodiment of the invention. The cross-linkers are designed to be specific for the receptor-ligand complex while having relatively no specificity for free receptor. Accordingly, it is possible not only to trap covalently the receptor, but also recover the excess receptor in unmodified form.

To accomplish this the invention provides:

1. A residue or "handle" common to all ligands on the solid support.
2. Heterobifunctional crosslinking agents in which one of the functionalities alkylates the "handle" kinetically much faster than it would alkylate either the receptor or the immobilized ligand.
3. The second functionality of the heterobifunctional crosslinker alkylating the immobilized receptor kinetically much faster than it would alkylate either the free receptor or the immobilized ligand.

According to one embodiment, the substrate is "doped" by replacing a small amount of the NVOC-aminocaproic acid reagent on the surface of the substrate with a small quantity of t-Boc-mercaptocaproic acid. The mercaptan would be blocked during all of subsequent peptide synthesis steps, but would deprotect upon exposure to acid. The surface would then be treated with receptor solution and the free sulfhydryl group acts as an outstanding nucleophile that is alkylated instantaneously upon treatment with a variety of commercially available heterobifunctional crosslinkers. In a second crosslinking step, alkylation of bound receptor is facile, because the proximity of the protein makes this reaction pseudo first-order. Nonspecific alkylation of free receptor would be a second-order process and therefore disfavored over specific alkylation. The excess receptor would then be removed and recovered by fast-desalting chromatography.

Because the receptor is now covalently bound to the substrate, subsequent processsing will not remove the receptor enabling detection of event those receptors with a high Kd.

C. Fluorescence Energy-Transfer Substrate Assays

A different application of the present invention tests for catalytic cleavage of various polymer sequences by an enzyme or other catalyst. For example, aspartyl proteases such as renin, HIV proteases, elastase, collagenase and some cathepsins can be tested against an array of peptides. According to this aspect of the invention, a variety of peptide sequences are synthesized on a solid substrate by the protection-deprotection strategy outlined above. The resulting array is probed with an enzyme which might cleave one or more peptide elements of the array resulting in a detectable chain.

Figure 12A:
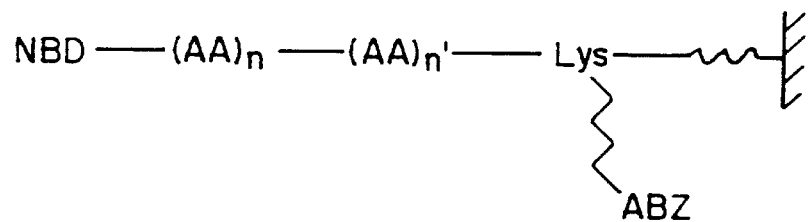
FIGS. 12A and 12B show a tripeptide used in a fluorescence energy-transfer substrate assay and that substrate after cleavage.
Figure 12B:
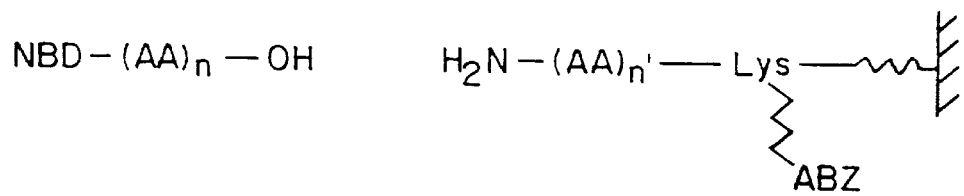

In one embodiment, the peptides to be tested have a fluorescence donor group such as 1-aminobenzoic acid (anthranilic acid or ABZ) or aminomethylcoumarin (AMC) located at one position on the peptide and a fluorescence quencher group such as lucifer yellow, methyl red or nitrobenzo-2-oxo-1,3-diazole (NBD) at a different position near the distal end of the peptide. Note, that some "donor" groups can also serve as "quencher" groups, depending on the relative excitation and emission frequencies of the particular pair selected. The intramolecular resonance energy transfer from the fluorescence donor molecule to the quencher will quench the fluorescence of the donor molecule. Upon cleavage, however, the quencher is separated from the donor group, leaving behind a fluorescent fragment. A scan of the surface with an epifluorescence microscope, for example, will show bright regions where the peptide has been cleaved. FIG. 12A shows a tripeptide having a donor-quencher pair on a substrate. The fluorescence donor molecule, 1-aminobenzoic acid (ABZ), is coupled to the ε-amino group of lysine (Lys) on the P' side of the substrate. The donor molecule could, of course, be attached to the α-amine group. A fluorescence quencher, NBD caproic acid, is coupled to the P side of the substrate molecule. Upon cleavage by a protease, as shown in FIG. 12B, the quencher is released leaving the fluorescent fragment still bound to the solid substrate for detection.

FIGS. 13A to 13H illustrate various alternative donor/quencher pairs which are used according to alternative embodiments of the invention.

IV. Examples

A. Example

The binding interactions of a monoclonal antibody D32.39, which was raised against the opioid peptide dynorphin B (YGGFLRRQFKVVT) SEQ ID NO: 3, were explored. The binding of antibody D32.39 to dynorphin B was previously shown to be directed to the carboxyl terminus. Initially, the experiment addressed the minimum peptide size required for binding and the location of the antibody binding epitope within the full length peptide. A binary masking strategy was used to generate an array of peptides of all the linear sequences contained within the terminal ten residues (FLRRQFKVVT). The ten-step synthesis was configured to yield four replicates of the 1024 possible compounds (i.e., 4096 distinct polymer synthesis regions), of which 1023 were peptides ranging in length from one to ten residues in length, with a mean length of five. This array includes every possible truncation and deletion sequence, as well as multiple deletions, contained within these ten residues, while preserving the linear order of amino acids. Due to the redundancy in amino acids (two valines, two arginines, and two phenylalanines), 560 unique sequences were generated.

After synthesis of the array, the terminal NVOC protecting groups were removed, the terminal amines were acetylated, and the side chain protecting groups were cleaved under standard conditions. Non-specific protein binding to the surface was blocked with 1% BSA/PBS/ 0.05% TWEEN 20™ (polyoxyethylenesorbitan monolaurate) detergent. The array was incubated with the D32.39 antibody at a concentration of 10 μg/ml for 2 hours, followed by reaction with 10 μg/ml of FITC conjugated anti-mounse antibody (Sigma) for 2 hours at 20° C. Following extensive washing with buffer, the array was scanned in a confocal fluorescence microscope with 488 nm excitation from an argon ion laser (Spectra-Physics). The resultant fluorescence image containing the intensity versus positional data for the array of peptides was normalized from 0 to 100% relative intensity by subtracting out background (the region within the array containing only the linker molecule) and using the region of highest intensity (FRQFKVVT) SEQ ID NO:4 as 100% relative intensity. The replicates were averaged, and the data sorted according to desired sequences. The entire screening process, including peptide synthesis and data acquisition and workup, required three days to complete.

Figure 14:
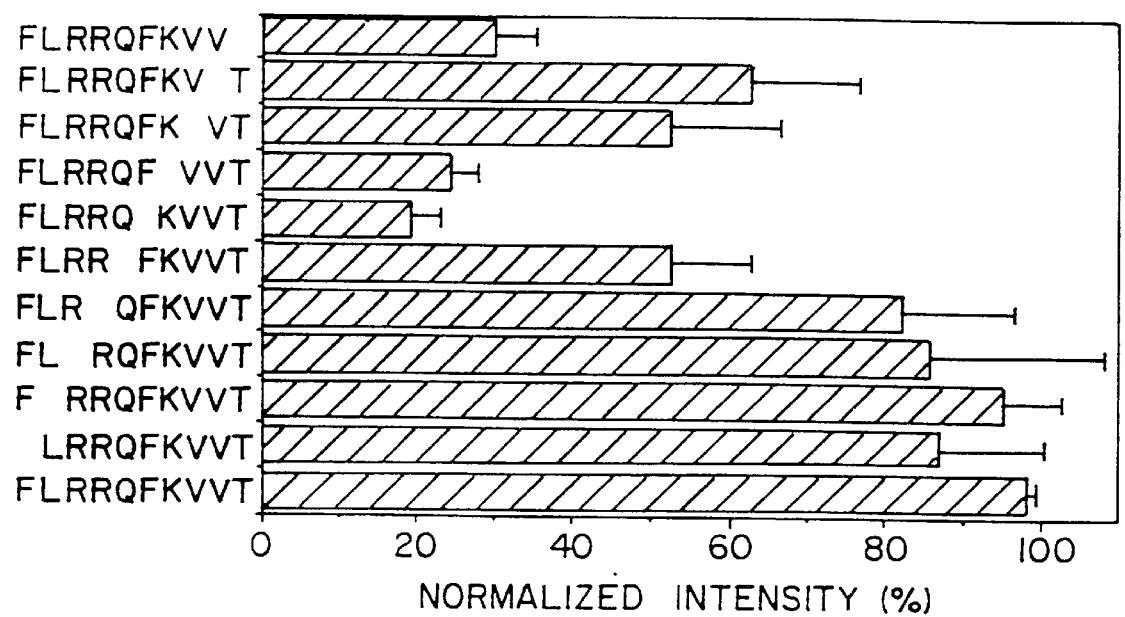
FIG. 14 illustrates sequence versus normalized fluorescence intensity for the ten possible single deletion peptides binding to the D32.39 antibody. A blank space represents a deleted amino acid relative to the full length kernel sequence (FLRRQFKVVT) SEQ ID NO: 1 shown on the bottom. Error bars represent the standard deviation of the averaged signals from four replicates. All peptides are acetylated on the amino terminus and are linked to the surface via an amide bond to the carboxyl terminus.

A survey of the data obtained from the ten possible single deletion peptides affords a preliminary estimate of the regions within the kernel sequence responsible for binding to the antibody. The normalized fluorescence intensity for each of these deletion sequences are is in FIG. 14. The full length peptide exhibited about 100% relative signal as anticipated, indicating that the epitope lay within the 10-mer sequence. Deletions in the kernel sequence near the amino terminus had little effect on the observed signal (compare F, L, R, R deletions), while deletions near the carboxyl terminus (compare F, K, T deletions) had a more pronounced effect. The antibody shows intermediate relative binding to both the valine and glutamine deletions.

Figure 15:
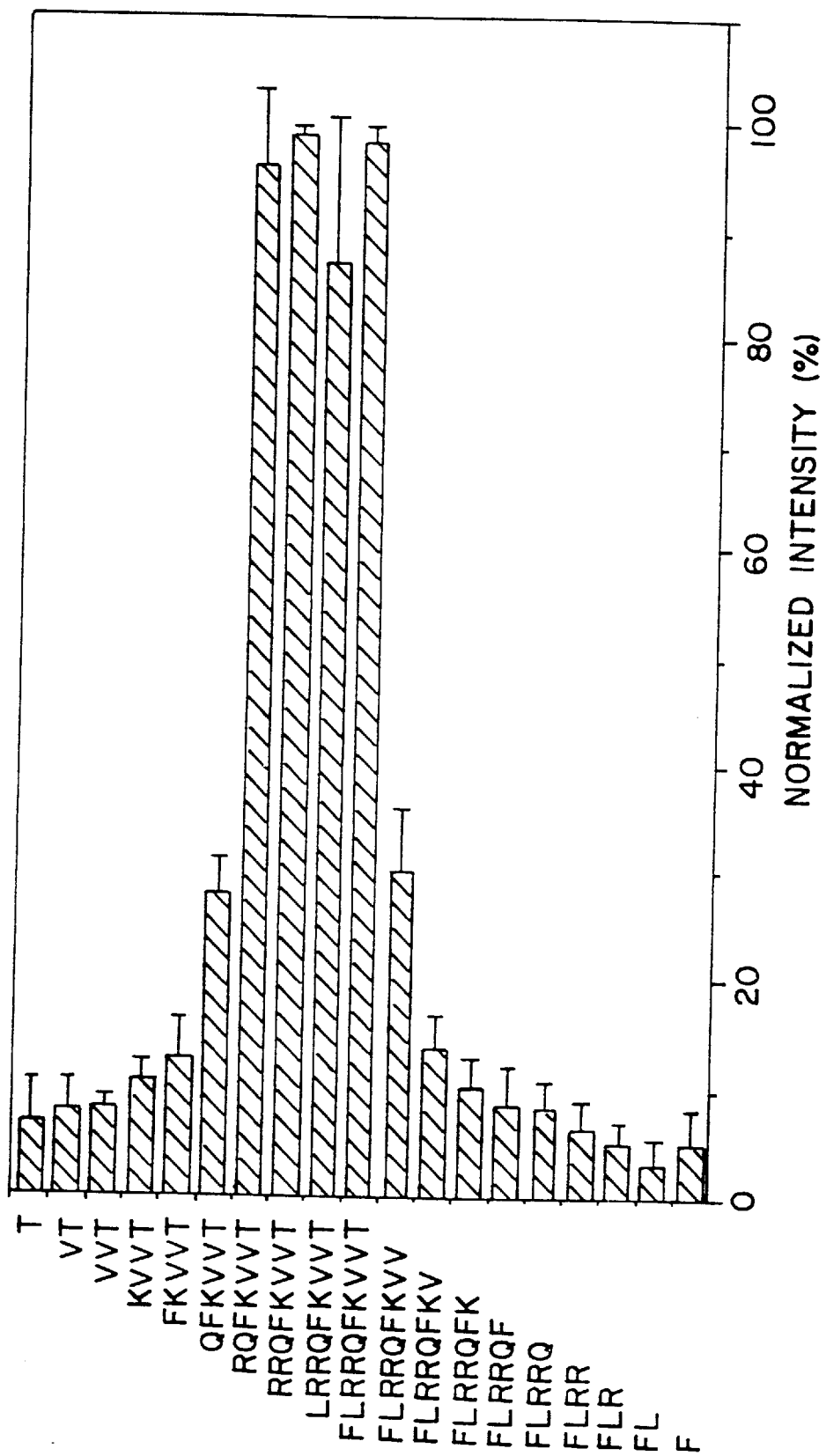
FIG. 15 illustrates sequence versus normalized fluorescence intensity for the terminally truncated peptides. The full length kernal sequence (FLRQFKVVT) SEQ ID NO: 2 is shown in the center of the graph. Error bars represent the standard deviation of the averaged signals from a minumum of four replicates. All peptides are acetylated on the amino terminus and are linked to the surface via an amide bond to the carboxyl terminus.

An analysis of the terminal truncated peptides generated in the array allows one to draw conclusions regarding the size and location of the epitope contained in the kernel sequence. The normalized fluorescence signals obtained for the terminal truncated peptides are shown in FIG. 15. The data reveals that truncations from the amino terminus are tolerated until loss of the second arginine residue, indicating the importance of the arginine residue to antibody recognition. Truncations from the carboxyl terminus are not tolerated as well, and the initial truncation of the threonine residue results in a large decrease in the observed fluorescence signal. The combination of these two observations predicts that the epitope lies between, and includes both, the arginine and threonine residues, or hence RQFKVVT SEQ ID NO: 5.

Examination of the signals observed for all the possible truncated sequences in Table 2 contained within the kernel sequence affords the highest degree of confidence in assigning the size and position of the epitope. Peptides shorter than seven residues were observed to show diminished binding to the antibody. Binding of the D32.39 antibody to the immobilized peptides exhibits a strong bias towards the RQFKVVT sequence.

TABLE 2

Sequence and Relative Fluorescence Intensities of the Truncated Dynorphin Peptides

| Sequence | Normalized Intensity (%)[a] |
|---|---|
| FLRRQFKVVT | 98 ± 1 |
| LRRQFKVVT SEQ ID NO: 6 | 87 ± 13 |
| FLRRQFKVV SEQ ID NO: 7 | 37 ± 15 |
| RRQFKVVT SEQ ID NO: 8 | 99 ± 1 |
| LRRQFKVV SEQ ID NO: 9 | 44 ± 12 |
| FLRRQFKV SEQ ID NO: 10 | 14 ± 3 |
| RQFKVVT SEQ ID NO: 11 | 99 ± 1 |
| RRQFKVV SEQ ID NO: 12 | 58 ± 10 |
| LRRQFKV SEQ ID NO: 13 | 16 ± 3 |
| FLRRQFK SEQ ID NO: 14 | 10 ± 3 |
| QFKVVT SEQ ID NO: 15 | 28 ± 3 |
| RQFKVV SEQ ID NO: 16 | 54 ± 11 |
| RRQFKV SEQ ID NO: 17 | 16 ± 3 |
| LRRQFK SEQ ID NO: 18 | 12 ± 3 |
| FLRRQF SEQ ID NO: 19 | 8 ± 3 |
| FKVVT SEQ ID NO: 20 | 13 ± 4 |
| QFKVV SEQ ID NO: 21 | 17 ± 2 |
| RQFKV SEQ ID NO: 22 | 16 ± 4 |
| RRQFK SEQ ID NO: 23 | 12 ± 3 |
| LRRQF SEQ ID NO: 24 | 10 ± 4 |
| FLRRQ SEQ ID NO: 25 | 8 ± 3 |
| KVVT SEQ ID NO: 26 | 11 ± 2 |
| FKVV SEQ ID NO: 27 | 10 ± 2 |
| QFKV SEQ ID NO: 28 | 11 ± 2 |
| RQFK SEQ ID NO: 29 | 13 ± 5 |
| RRQF SEQ ID NO: 30 | 11 ± 5 |
| LRRQ SEQ ID NO: 31 | 10 ± 4 |
| FLRR SEQ ID NO: 32 | 6 ± 3 |

[a]Errors were standard deviations of the averaged signals from a minimum of four replicates. All peptides were acetylated on the amino terminus and were linked to the surface via an amide bond to the carboxyl terminus.

To confirm the interpretation of the observed fluorescence signals, peptides synthesized on a conventional solid phase peptide synthesizer were tested. The $IC_{50}$ values for the competition of free peptide against radiolabeled dynorphin B peptide were determined and are tabulated in Table 3. There is a striking correlation between the rank ordering of the relative fluorescence intensity and the solution $IC_{50}$ values. Although the antibody appears to require the presence of the threonine residue at the carboxyl terminus, it shows little preference for the free carboxamide versus the free acid.

TABLE 3

Solution Binding Data for the
Dynorphin Peptides to the D32.39 Antibody

| Sequence | IC$_{50}$ ($\mu$M)[a] | Normalized Intensity (%)[b] |
|---|---|---|
| YGGFLRRQFKVVT—OH | 0.0057 | nd[c] |
| Ac-FLRRQFKVVT—OH | nd | 98 |
| Ac-RRQFKVVT—OH | 0.0039 | 99 |
| Ac-RQFKVVT—OH | 0.011 | 99 |
| Ac-RQFKVVT-NH$_2$ | 0.0073 | — |
| Ac-QFKVVT—OH | 3.2 | 28 |
| Ac-FKVVT—OH | 77.0 | 13 |

[a]The IC$_{50}$ values were determined by competition against radiolabeled dynorphin B peptide.
[b]The normalized intensity refers to the relative fluorescence intensity observed from the corresponding surface-immobilized peptides. All surface-immobilized peptides were acetylated on the amino terminus and were linked to the surface via an amide bond to the carboxyl terminus.
[c]Not determined.

The relative fluorescence intensity observed for biological recognition of an antibody to an array of immobilized peptides depends on several factors. Of primary importance is the multivalent interaction between the antibody and the surface due to the presence of two antibody combining sites in an IgG molecule. If the peptide chains are spaced relatively close on a surface, then the antibody can span two chains and the observed effective binding constant may be greater than the monovalent value. Estimates of the surface density of the reactive peptide chains on the surface suggest that this is likely to occur. In addition, the situation here is even more complex because a second bivalent antibody was used to detect the initial binding of D32.39.

With the size and position of the epitope thus determined, the present invention was used to examine novel substitutions in the RQFKVVT peptide sequence. The methods of the invention allowed systematic replacement at each position in the lead sequence by other amino acids. A schematic of the substitutions is shown in Table 4, where X represents the position undergoing substitution. When x is the 20 L-amino acids, the array comprised 140 peptides which were synthesized and screened for binding. The masking technique illustrated in FIGS. 1A–1C with a translated, full-size mask, as shown in step 2 of FIG. 1A, was utilized. Preliminary results identified Q, K, V, and T as the residues most amenable to substitution.

TABLE 4

| Schematic of Illustrative Single Substitutions into the RQFKVVT Peptide Sequence |
|---|
| XQFKVVT[a] |
| RXFKVVT |
| RQXKVVT |
| RQFXVVT |
| RQFKXVT |
| RQFKVXT |
| RQFKVVX |

[a]X represents the position undergoing substitution.

These results demonstrate the application of a novel technique employing both photolithography and solid phase peptide chemistry to create arrays of spatially-addressable chemical libraries. The ability to screen simultaneously all the immobilized peptides for binding to a biological target allows one to generate powerful structure activity relationship (SAR) databases. The use of novel building blocks as a tool to impart desirable physical properties into the arrays should aid in the optimization of new lead compounds in the area of drug discovery.

B. Example

The example below illustrates aspects of one methodology for the formation of cyclic polymers. The method may be used to construct arrays of cyclic polymers according to the above methods.

Eight slides derivatized with NVOC-aminocaproic acid were photodeprotected for ten minutes in 5 mM sulfuric acid/dioxane using 365 nm light. After neutralization of the surface, six of the slides were exposed to 0.1M BOP activated NVOC-Glu(O-t-butyl)-OH, while the remaining two slides were exposed to 0.1M BOP activated NVOC-Glu-OFm. The first six slides were divided into three groups and each group was derivatized with either BOP activated Boc-Pro-Pro-Pro-Pro-OH, SEQ ID NO: 33 Boc-Ala-Ala-Ala-Ala-OH, SEQ ID NO: 34 or Boc-Ala-Gly-Gly-Gly-OH. SEQ ID NO: 35 The second two slides from above were derivatized with BOP activated Boc-Val-Val-Val-Val-OH. SEQ ID NO: 36 This gave four pairs of slides, each with a pentapeptide on the surface with a side chain carboxyl (still protected) with which to cyclize. Each slide was deprotected with TFA to remove the Boc and t-butyl groups (from both the amino terminus and the masked carboxyl group), and then the two slides with Fm as a protecting group were treated with piperidine to unmask the carboxyl group.

A sixteen-well template was placed on each slide in order to physically segregate different regions of the surface and one member of each pair was warmed (either to 41° or 44° C.) while the second member was kept at 20° C. during the following reactions. Each well of the template was treated with either a 0.1M solution of activator or solvent for 4.5 hours. The activators were BOP, HBTU, and diphenylphosphoryl azide (DPPA). After the specified time, the wells were washed and the templates removed. The slides were stained with a 10 mM solution of a 9:1 mixture of phenyl isothiocyanate (PITC): fluorescein isothiocyanate (FITC). The slides were washed and scanned for fluorescence using a confocal microscope.

Cyclization of the peptides was expected to result in the loss of reactivity of the terminal amine, and hence, the loss of fluorescence intensity. Cyclization efficiency was measured as the decrease in fluorescence intensity for the peptides that had been treated with an activator as compared to untreated peptides. Cyclization was found to occur readily in all cases. The activators BOP and HBTU were found to be more effective than DPPA. Temperature had little effect on the cyclization efficiency.

V. Conclusion

The above description is illustrative and not restrictive. Many variations of the invention will become apparent to those of skill in the art upon review of this disclosure. Merely by way of example, while the invention is illustrated primarily with regard to peptide, oligosaccharide and nucleotide synthesis, the invention is not so limited. By way of another example, while the detection apparatus has been illustrated primarily herein with regard to the detection of marked receptors, the invention will find application in other areas. For example, the detection apparatus disclosed herein could be used in the fields of catalysis, DNA or protein gel scanning, and the like. The scope of the invention should, therefore, be determined not with reference to the above description, but instead should be determined with reference to the appended claims along with their full scope of equivalents.

What is claimed is:

1. An array of cyclic nucleic acids on a substrate, said nucleic acids having N nucleotide positions, said substrate comprising N different sites, said substrate sites comprising said cyclic nucleic acids coupled thereto, said cyclic nucleic acids comprising common nucleotide sequences but coupled to said substrate at a different one of said nucleotide positions via a tether molecule in each of said different substrate sites.

2. An array as recited in claim 1 wherein said nucleic acids are coupled to said substrate via a common tether molecule.

3. An array as recited in claim 2 wherein said tether molecule substitutes for a different one of said nucleotides in said common nucleotide sequence within each of said different sites.

4. An array as recited in claim 2 wherein said common tether molecule is inserted between two of said nucleotide positions in said common nucleotide sequence at a different position within each of said different substrate sites.

5. An array of cyclic polypeptides on a substrate, said polypeptides having N amino acid positions, said substrate comprising N different sites, said substrate sites comprising said cyclic polypeptides coupled thereto, said cyclic polypeptides comprising common amino acid sequences but coupled to said substrate at a different one of said amino acid positions via a tether molecule in each of said different substrate sites.

6. An array as recited in claim 5 wherein said tether molecule forms a disulfide bond in said cyclic polypeptides.

7. An array as recited in claim 5 wherein said tether molecule is glutamic acid.

8. An array as recited in claim 5 wherein said polypeptides are coupled to said substrate via a common tether molecule.

9. An array as recited in claim 8 wherein said tether molecule substitutes for a different one of said amino acid in said common amino acid sequence within each of said different sites.

10. An array as recited in claim 8 wherein said common tether molecule is inserted between two of said amino acid positions in said common amino acid sequence at a different position within each of said different substrate sites.

* * * * *